(12) United States Patent
Ma et al.

(10) Patent No.: US 10,661,448 B2
(45) Date of Patent: May 26, 2020

(54) BIOMIMETIC LIMB AND ROBOT USING THE SAME

(71) Applicants: Tsinghua University, Beijing (CN); HON HAI PRECISION INDUSTRY CO., LTD., New Taipei (TW)

(72) Inventors: He Ma, Beijing (CN); Yang Wei, Beijing (CN); Kai Liu, Beijing (CN); Kai-Li Jiang, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 223 days.

(21) Appl. No.: 15/713,987

(22) Filed: Sep. 25, 2017

(65) Prior Publication Data

US 2018/0099416 A1 Apr. 12, 2018

(30) Foreign Application Priority Data

Oct. 12, 2016 (CN) .......................... 2016 1 0890498

(51) Int. Cl.
*A61F 2/58* (2006.01)
*F03G 7/06* (2006.01)
(Continued)

(52) U.S. Cl.
CPC ............ *B25J 15/024* (2013.01); *A61F 2/583* (2013.01); *A61F 2/586* (2013.01); *B82B 1/005* (2013.01); *H02N 10/00* (2013.01); *A61F 2002/543* (2013.01); *B82Y 15/00* (2013.01); *B82Y 30/00* (2013.01); *B82Y 40/00* (2013.01); *F03G 7/06* (2013.01); *Y10S 977/742* (2013.01); *Y10S 977/778* (2013.01); *Y10S 977/811* (2013.01);
(Continued)

(58) Field of Classification Search
CPC ... F03G 7/06; H02N 10/00; A61F 2/58; A61F 2/586
See application file for complete search history.

(56) References Cited

U.S. PATENT DOCUMENTS

2010/0314617 A1 12/2010 Ito
2011/0094217 A1 4/2011 Chen et al.
(Continued)

FOREIGN PATENT DOCUMENTS

CN 101886261 11/2010
CN 105428516 3/2016
(Continued)

OTHER PUBLICATIONS

Tongyu Wang et al. "Increasing Efficiency, Speed, and Responsivity of Vanadium Dioxide Based Photothermally Driven Actuators Using Single-Wall Carbon Nanotube Thin-Films" ACS nano, vol. 9, No. 4, Apr. 8, 2015, pp. 4371-4378.

*Primary Examiner* — Bruce E Snow
(74) *Attorney, Agent, or Firm* — ScienBiziP, P.C.

(57) ABSTRACT

The disclosure relates to a biomimetic limb and robot using the same. The biomimetic limb includes: an arm and a biomimetic hand connected to the arm and including at least one biomimetic finger. The biomimetic finger includes a carbon nanotube layer and a vanadium dioxide layer ($VO_2$) layer stacked with each other. Because the drastic, reversible phase transition of $VO_2$, the biomimetic finger has giant deformation amplitude and fast response. An robot using the biomimetic limb is also provided.

20 Claims, 18 Drawing Sheets

(51) Int. Cl.
- *H02N 10/00* (2006.01)
- *B25J 15/02* (2006.01)
- *B82B 1/00* (2006.01)
- *A61F 2/54* (2006.01)
- *B82Y 30/00* (2011.01)
- *B82Y 15/00* (2011.01)
- *B82Y 40/00* (2011.01)

(52) U.S. Cl.
CPC ........ *Y10S 977/833* (2013.01); *Y10S 977/891* (2013.01); *Y10S 977/948* (2013.01)

(56) References Cited

U.S. PATENT DOCUMENTS

| | | |
|---|---|---|
| 2014/0238013 A1 | 8/2014 | Wu et al. |
| 2016/0025078 A1 | 1/2016 | Li et al. |
| 2016/0025079 A1 | 1/2016 | Li et al. |

FOREIGN PATENT DOCUMENTS

| | | |
|---|---|---|
| JP | 2008-57470 A | 3/2008 |
| JP | 2011-91994 | 5/2011 |
| JP | 2016-25837 A | 2/2016 |
| JP | 2016-88827 | 5/2016 |
| JP | 2016-88827 A | 5/2016 |
| JP | 2016-160148 | 9/2016 |
| TW | I553921 | 10/2016 |

BIOMIMETIC LIMB AND ROBOT USING THE SAME

CROSS-REFERENCE TO RELATED APPLICATIONS

This application claims all benefits accruing under 35 U.S.C. § 119 from China Patent Application No. 201610890498.2, filed on Oct. 12, 2016, in the China Intellectual Property Office, the disclosure of which is incorporated herein by reference. This application is related to applications entitled, "ACTUATOR BASED ON CARBON NANOTUBES AND ACTUATING SYSTEM USING THE SAME", filed on Sep. 25, 2017, with application Ser. No. 15/713,924, "METHOD FOR MAKING AN ACTUATOR BASED ON CARBON NANOTUBES", filed on Sep. 25, 2017, with application Ser. No. 15/713,945, "TEMPERATURE SENSITIVE SYSTEM", filed on Sep. 25, 2017, with application Ser. No. 15/713,996, and "BIOMIMETIC INSECT", filed on Sep. 25, 2017, with application Ser. No. 15/714,004.

BACKGROUND

1. Technical Field

The present disclosure relates to actuators, especially, an actuator based on carbon nanotubes (CNT) and applications using the same.

2. Description of Related Art

The actuator is a device used to convert the other energy into mechanical energy. The type of the actuator usually includes electrostatic drive actuator, magnetic drive actuator, and thermal drive actuator, such as electro-thermal actuator. Conventional electro-thermal actuator is a membrane structure of which main material is polymer. When a current is applied, a temperature of the polymer is increased, which can lead to a sensible volume expansion of the polymer, and then the membrane structure bends and the electro-thermal actuator is activated. Thus, electrode materials of the electro-thermal actuator are required to be excellent conductive, flexible, and thermally stable due to its operating principle.

Composite materials containing carbon nanotubes are conductive and already being used for electro-thermal actuator. When a current is applied, the electro-thermal composite materials containing carbon nanotubes can generate heat. Then a volume of the electro-thermal composite materials is expanded and the electro-thermal composite materials bends. Conventional electro-thermal composite materials include a flexible polymer matrix and carbon nanotubes dispersed in the flexible polymer matrix. However, deformation of conventional electro-thermal composite materials is not large enough, and a response rate of conventional electro-thermal composite materials is slow. Improvement in the art is preferred.

What is needed, therefore, is an actuator based on carbon nanotubes and applications using the same that overcomes the problems as discussed above.

BRIEF DESCRIPTION OF THE DRAWINGS

Many aspects of the exemplary embodiments can be better understood with reference to the following drawings. The components in the drawings are not necessarily drawn to scale, the emphasis instead being placed upon clearly illustrating the principles of the exemplary embodiments. Moreover, in the drawings, like reference numerals designate corresponding parts throughout the several views.

DETAILED DESCRIPTION

Figure 1:
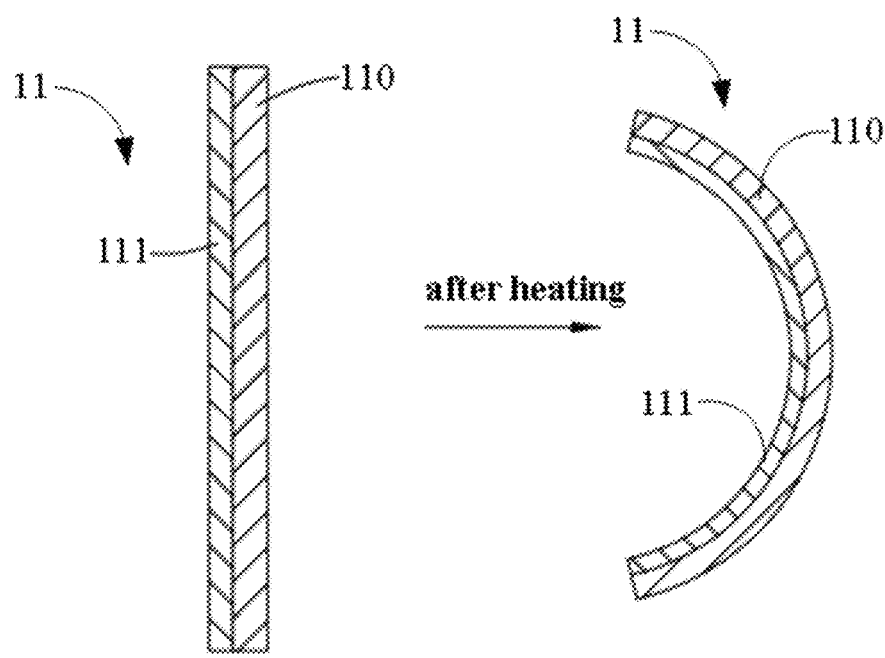
FIG. 1 is a sectional view of a first exemplary embodiment of an actuator.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein can be practiced without these specific details. In other instances, methods, procedures, and components have not been described in detail so as not to obscure the related relevant feature being described. The drawings are not necessarily to scale, and the proportions of certain parts may be exaggerated better illustrate details and features. The description is not to considered as limiting the scope of the exemplary embodiments described herein.

Several definitions that apply throughout this disclosure will now be presented. The term "coupled" is defined as connected, whether directly or indirectly through intervening components, and is not necessarily limited to physical connections. The connection can be such that the objects are permanently connected or releasably connected. The term "outside" refers to a region that is beyond the outermost confines of a physical object. The term "inside" indicates that at least a portion of a region is partially contained within a boundary formed by the object. The term "substantially" is defined to essentially conforming to the particular dimension, shape or other word that substantially modifies, such that the component need not be exact. For example, substantially cylindrical means that the object resembles a cylinder, but can have one or more deviations from a true cylinder. The term "comprising" means "including, but not necessarily limited to"; it specifically indicates open-ended inclusion or membership in a so-described combination, group, series and the like. It should be noted that references to "an" or "one" exemplary embodiment in this disclosure are not necessarily to the same exemplary embodiment, and such references mean at least one.

References will now be made to the drawings to describe, in detail, various exemplary embodiments of the present actuators based on carbon nanotubes and applications using the same.

Referring to FIG. 1, a first exemplary embodiment of an actuator 11 is provided. The actuator 11 includes a carbon nanotube layer 110 and a vanadium dioxide ($VO_2$) layer 111 stacked with each other to form a $VO_2$/Carbon Nanotube (CNT) composite. The carbon nanotube layer 110 generates heat to heat the vanadium dioxide layer 111 or absorbs heat and transfer the heat to the vanadium dioxide layer 111. The vanadium dioxide layer 111 would shrink along in-plane directions that are perpendicular to the thickness direction of the vanadium dioxide layer 111. Thus, the actuator 11 bends. Because the carbon nanotube layer 110 has a higher and faster light-heat conversion efficiency and electric-heating conversion efficiency, and lower specific heat capacity, the actuator 11 has a faster response rate.

The thickness of the vanadium dioxide layer 111 is not limited and can be selected according to need. The thickness of the vanadium dioxide layer 111 can be in a range of about 100 nanometers to about 500 micrometers. In one exemplary embodiment, the thickness of the vanadium dioxide layer 111 can be in a range of about 1 micrometer to about 10 micrometers. When the thickness of the vanadium dioxide layer 111 is 150 nanometers, the visible light transmittance of the vanadium dioxide layer 111 is about 40%. The phase transformation temperature of the vanadium dioxide layer 111 is 68° C. The vanadium dioxide layer 111, consisting of pure vanadium dioxide, has an insulating phase at a temperature lower than 68° C., such as room temperature of 20° C. to 25° C. When the vanadium dioxide layer 111 is heated to phase transformation temperature, such as above 68° C., the insulating phase is transited to metallic phase. Transiting from the insulating phase to the metallic phase, the vanadium dioxide layer 111 shrinks along the c axis, that is a crystallographic axis, of the metallic phase, resulting in a spontaneous strain E as high as 1-2%. A volumetric work density of the vanadium dioxide layer 111 at metallic phase is about 7 $J/cm^3$-28 $J/cm^3$, and an elastic modulus of the vanadium dioxide layer 111 at metallic phase is about 140 GPa. When the vanadium dioxide layer 111 is transitioning from the insulating phase to the metallic phase, the resistance of the $VO_2$/CNT composite decreases by 11%. Because the volume of the carbon nanotube layer 110 is unchanged, when the vanadium dioxide layer 111 shrinks, the actuator 11 bends toward the side of the vanadium dioxide layer 111. When the vanadium dioxide layer 111 is cooled to a low temperature, such room temperature, the metallic phase is transited to the insulating phase. The actuator 11 is stretched to the original state, such as planar or curved. The actuator 11 can bend from the planar shape to a curved shape, or bend from a first curved shape with a large radius of curvature to a second curved shape with a small radius of curvature.

The vanadium dioxide layer 111 can also be a doped vanadium dioxide film. The phase transformation temperature of the vanadium dioxide layer 111 can be changed by doping. The doping element can be tungsten, molybdenum, aluminum, phosphorus, niobium, thallium, or fluorine. The doping percentage can be 0.5%-5%. When the doping element has large-scale atom, such as tungsten or molybdenum, the phase transformation temperature of the vanadium dioxide layer 111 can be reduced. When the doping element has small-scale atom, such as aluminum or phosphorus, the phase transformation temperature of the vanadium dioxide layer 111 can be increased. In one exemplary embodiment, the vanadium dioxide layer 111 is a doped with 1.5% tungsten. The phase transformation temperature of the vanadium dioxide layer 111 is reduced to 34° C. When the tungsten doped vanadium dioxide layer 111 is transitioning from the insulating phase to the metallic phase, the resistance of the tungsten doped $VO_2$/CNT composite decreases by 6.8%.

The carbon nanotube layer 110 includes a plurality of carbon nanotubes. The carbon nanotubes in the carbon nanotube layer 110 can be single-walled, double-walled, or multi-walled carbon nanotubes. The length and diameter of the carbon nanotubes can be selected according to need. The thickness of the carbon nanotube layer 110 can be in a range of about 100 nanometer to about 100 micrometers. For example, the thickness of the carbon nanotube layer 110 can be in a range of about 1 micrometer to 10 micrometers.

The carbon nanotubes in the carbon nanotube layer 110 can be orderly arranged to form an ordered carbon nanotube structure or disorderly arranged to form a disordered carbon nanotube structure. The term 'disordered carbon nanotube structure' includes, but is not limited to, a structure where the carbon nanotubes are arranged along many different directions, and the aligning directions of the carbon nanotubes are random. The number of the carbon nanotubes arranged along each different direction can be almost the same (e.g. uniformly disordered). The disordered carbon nanotube structure can be isotropic. The carbon nanotubes in the disordered carbon nanotube structure can be entangled with each other. The term 'ordered carbon nanotube structure' includes, but is not limited to, a structure where the carbon nanotubes are arranged in a consistently systematic manner, e.g., the carbon nanotubes are arranged approximately along a same direction and/or have two or more sections within each of which the carbon nanotubes are arranged approximately along a same direction (different sections can have different directions).

In one exemplary embodiment, the carbon nanotubes in the carbon nanotube layer 110 are arranged to extend along the direction substantially parallel to the surface of the carbon nanotube layer 110. In one exemplary embodiment, the carbon nanotube layer 110 is a free-standing structure and can be drawn from a carbon nanotube array. The term "free-standing structure" means that the carbon nanotube layer 110 can sustain the weight of itself when it is hoisted by a portion thereof without any significant damage to its structural integrity. Thus, the carbon nanotube layer 110 can be suspended by two spaced supports.

The carbon nanotube layer 110 can be a substantially pure structure of carbon nanotubes, with few impurities and chemical functional groups. The carbon nanotube layer 110 can also be a composite including a carbon nanotube matrix and non-carbon nanotube materials. The non-carbon nanotube materials can be graphite, graphene, silicon carbide, boron nitride, silicon nitride, silicon dioxide, diamond, amorphous carbon, metal carbides, metal oxides, or metal nitrides. The non-carbon nanotube materials can be coated on the carbon nanotubes in the carbon nanotube layer 110 or filled in the apertures of the carbon nanotube layer 110. In one exemplary embodiment, the non-carbon nanotube materials are coated on the carbon nanotubes in the carbon nanotube layer 110. The non-carbon nanotube materials can be deposited on the carbon nanotubes in the carbon nanotube layer 110 by chemical vapor deposition (CVD) or physical vapor deposition (PVD), such as sputtering.

The carbon nanotube layer 110 can include at least one carbon nanotube film, at least one carbon nanotube wire, or combination thereof. In one exemplary embodiment, the carbon nanotube layer 110 can include a single carbon nanotube film or two or more carbon nanotube films stacked together. Thus, the thickness of the carbon nanotube layer 110 can be controlled by the number of the stacked carbon nanotube films. The number of the stacked carbon nanotube films is not limited. In one exemplary embodiment, the carbon nanotube layer 110 can include a layer of parallel and spaced carbon nanotube wires. Also, the carbon nanotube layer 110 can include a plurality of carbon nanotube wires crossed or weaved together to form a carbon nanotube net. The distance between two adjacent parallel and spaced carbon nanotube wires can be in a range of about 0.1 micrometers to about 200 micrometers. In one exemplary embodiment, the distance between two adjacent parallel and spaced carbon nanotube wires is in a range of about 10 micrometers to about 100 micrometers. The gap between two adjacent substantially parallel carbon nanotube wires is defined as the aperture. The size of the aperture can be controlled by controlling the distance between two adjacent parallel and spaced carbon nanotube wires. The length of the gap between two adjacent parallel carbon nanotube wires can be equal to the length of the carbon nanotube wire. It is understood that any carbon nanotube structure described can be used with all exemplary embodiments.

Figure 3:
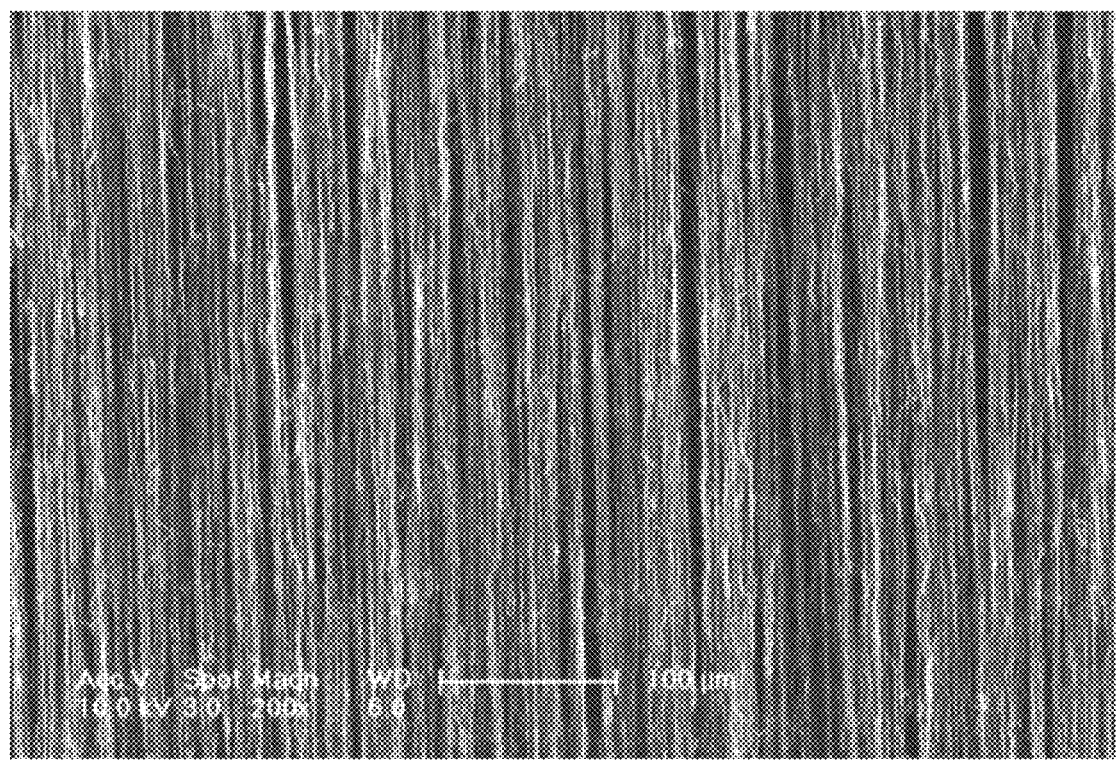
FIG. 3 is a Scanning Electron Microscope (SEM) image of a drawn carbon nanotube film.
Figure 4:
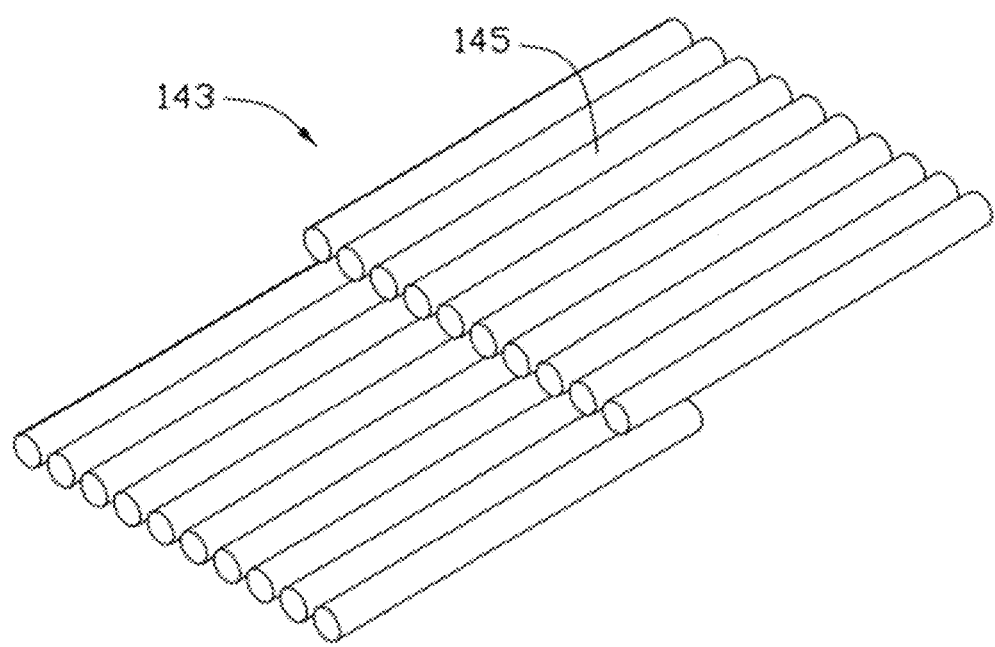
FIG. 4 is a schematic view of a carbon nanotube segment of the drawn carbon nanotube film of FIG. 3.

In one exemplary embodiment, the carbon nanotube layer 110 includes at least one drawn carbon nanotube film. A drawn carbon nanotube film can be drawn from a carbon nanotube array that is able to have a film drawn therefrom. The drawn carbon nanotube film includes a plurality of successive and oriented carbon nanotubes joined end-to-end by van der Waals attractive force therebetween. The drawn carbon nanotube film is a free-standing film. Referring to FIGS. 3 to 4, each drawn carbon nanotube film includes a plurality of successively oriented carbon nanotube segments 143 joined end-to-end by van der Waals attractive force therebetween. Each carbon nanotube segment 143 includes a plurality of carbon nanotubes 145 parallel to each other, and combined by van der Waals attractive force therebetween. As can be seen in FIG. 3, some variations can occur in the drawn carbon nanotube film. The carbon nanotubes 145 in the drawn carbon nanotube film are oriented along a preferred orientation. The drawn carbon nanotube film can be treated with an organic solvent to increase the mechanical strength and toughness and reduce the coefficient of friction of the drawn carbon nanotube film. A thickness of the drawn carbon nanotube film can range of about 0.5 nanometers to about 100 micrometers.

The carbon nanotube layer 110 can include at least two stacked drawn carbon nanotube films. In other exemplary embodiments, the carbon nanotube layer 110 can include two or more coplanar carbon nanotube films, and can include layers of coplanar carbon nanotube films. Additionally, when the carbon nanotubes in the carbon nanotube film are aligned along one preferred orientation (e.g., the drawn carbon nanotube film), an angle can exist between the orientation of carbon nanotubes in adjacent films, whether stacked or adjacent. Adjacent carbon nanotube films can be combined by only the van der Waals attractive force therebetween. An angle between the aligned directions of the carbon nanotubes in two adjacent carbon nanotube films can range of about 0 degrees to about 90 degrees. When the angle between the aligned directions of the carbon nanotubes in adjacent stacked drawn carbon nanotube films is larger than 0 degrees, a plurality of micropores is defined by the carbon nanotube layer 110. In one exemplary embodiment, the carbon nanotube layer 110 includes 50 drawn carbon nanotube films stacked with each other.

In another exemplary embodiment, the carbon nanotube layer 110 can include a pressed carbon nanotube film. The pressed carbon nanotube film can be a free-standing carbon nanotube film. The carbon nanotubes in the pressed carbon nanotube film are arranged along a same direction or arranged along different directions. The carbon nanotubes in the pressed carbon nanotube film can rest upon each other. Adjacent carbon nanotubes are attracted to each other and combined by van der Waals attractive force. An angle between a primary alignment direction of the carbon nanotubes and a surface of the pressed carbon nanotube film is about 0 degrees to approximately 15 degrees. The greater the pressure applied, the smaller the angle formed. If the carbon nanotubes in the pressed carbon nanotube film are arranged along different directions, the carbon nanotube layer 110 can be isotropic.

In another exemplary embodiment, the carbon nanotube layer 110 includes a flocculated carbon nanotube film. The flocculated carbon nanotube film can include a plurality of long, curved, disordered carbon nanotubes entangled with each other. Furthermore, the flocculated carbon nanotube film can be isotropic. The carbon nanotubes can be substantially uniformly dispersed in the carbon nanotube film. Adjacent carbon nanotubes are acted upon by van der Waals attractive force to form an entangled structure with micropores defined therein. Sizes of the micropores can be less than 10 micrometers. The porous nature of the flocculated carbon nanotube film increases the specific surface area of the carbon nanotube layer 110. Further, due to the carbon nanotubes in the carbon nanotube layer 110 being entangled with each other, the carbon nanotube layer 110 employing the flocculated carbon nanotube film has excellent durability, and can be fashioned into desired shapes with a low risk to the integrity of the carbon nanotube layer 110. The flocculated carbon nanotube film, in some exemplary embodiments, is free-standing due to the carbon nanotubes being entangled and adhered together by van der Waals attractive force therebetween.

The carbon nanotube wire can be untwisted or twisted. Treating the drawn carbon nanotube film with a volatile organic solvent can form the untwisted carbon nanotube wire. Specifically, the organic solvent is applied to soak the entire surface of the drawn carbon nanotube film. During the soaking, adjacent parallel carbon nanotubes in the drawn carbon nanotube film bundle together, due to the surface tension of the organic solvent as it volatilizes, and thus, the drawn carbon nanotube film shrinks into an untwisted carbon nanotube wire. The untwisted carbon nanotube wire includes a plurality of carbon nanotubes substantially oriented along a same direction (i.e., a direction along the length of the untwisted carbon nanotube wire). The carbon nanotubes are substantially parallel to the axis of the untwisted carbon nanotube wire. More specifically, the untwisted carbon nanotube wire includes a plurality of successive carbon nanotube segments joined end to end by van der Waals attractive force therebetween. Each carbon nanotube segment includes a plurality of carbon nanotubes substantially parallel to each other, and combined by van der Waals attractive force therebetween. The carbon nanotube segments can vary in width, thickness, uniformity, and shape. The length of the untwisted carbon nanotube wire can be arbitrarily set as desired. A diameter of the untwisted carbon nanotube wire ranges from about 0.5 nanometers to about 100 micrometers.

The twisted carbon nanotube wire can be formed by twisting a drawn carbon nanotube film using a mechanical force to turn the two ends of the drawn carbon nanotube film in opposite directions. The twisted carbon nanotube wire includes a plurality of carbon nanotubes helically oriented around an axial direction of the twisted carbon nanotube wire. More specifically, the twisted carbon nanotube wire includes a plurality of successive carbon nanotube segments joined end to end by van der Waals attractive force therebetween. Each carbon nanotube segment includes a plurality of carbon nanotubes parallel to each other, and combined by van der Waals attractive force therebetween. The length of the carbon nanotube wire can be set as desired. A diameter of the twisted carbon nanotube wire can be from about 0.5 nanometers to about 100 micrometers. Further, the twisted carbon nanotube wire can be treated with a volatile organic solvent after being twisted to bundle the adjacent paralleled carbon nanotubes together. The specific surface area of the twisted carbon nanotube wire will decrease, while the density and strength of the twisted carbon nanotube wire will increase.

Figure 2:
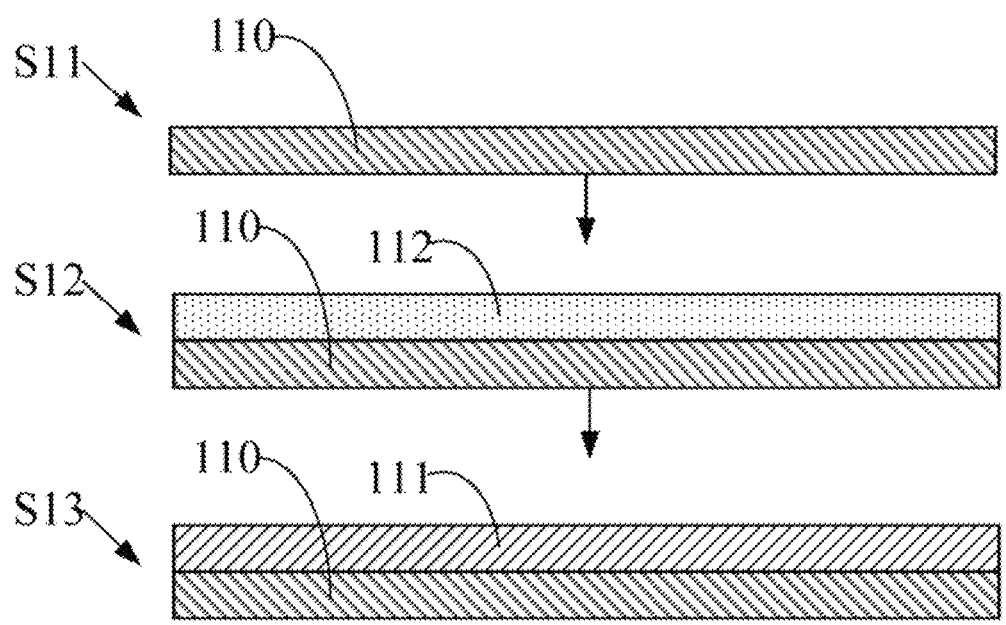
FIG. 2 is a flowchart showing a first exemplary embodiment of a method for making the actuator of FIG. 1.

Referring to FIG. 2, a method for making the actuator 11 of the first exemplary embodiment comprises:

step (S11), providing the carbon nanotube layer 110;

step (S12), depositing a $VO_x$ layer 112 on the carbon nanotube layer 110 to form a $VO_x$/CNT composite; and step (S13), annealing the $VO_x$/CNT composite in low-pressure oxygen atmosphere to form a $VO_2$/CNT composite, where the $VO_x$ layer 112 is transformed to the vanadium dioxide layer 111.

In step (S12), the method for depositing the $VO_x$ layer 112 is not limited and can be CVD or magnetron sputtering. In step (S13), the oxygen atmosphere can be pure oxygen gas or air.

In one exemplary embodiment, the carbon nanotube layer 110 is formed by cross stacking 50 drawn carbon nanotube films of FIGS. 3-4. The $VO_x$ layer 112 is deposited on a surface of the 50-layer cross-stacked drawn carbon nanotube films by DC magnetron sputtering. The DC magnetron sputtering system has a high-purity vanadium metal target. The sputtering is carried out with flowing gas mixtures of 49.7 standard cubic centimeter per minute (sccm) Ar and 0.3 sccm $O_2$, under 0.55 Pa, for 30 minutes, at DC power of 60 W, and at room temperature. After the $VO_x$ layer 112 deposition, the $VO_x$/CNT composite is annealed in low-pressure pure $O_2$ atmosphere under $3 \times 10^{-2}$ mbar at 450° C. for 10 minutes to crystallize into a $VO_2$/CNT composite. The $VO_x$/CNT composite can be annealed by heating in a furnace, or applying an electronic current to the carbon nanotube layer 110 to heat the $VO_x$ layer 112. When the annealing is performed at a temperature above 500° C., the annealing is performed in a vacuum room filled with trace oxygen. Thus, the carbon nanotube layer 110 can be prevented from being oxidized. In one exemplary embodiment, the oxygen gas is introduced in to the vacuum room at a flow rate less than 2 sccm. When the annealing is performed at a temperature below 450° C., the annealing can be performed in air.

There is a lattice mismatch between the vanadium dioxide and carbon nanotubes. When the $VO_x$ layer 112 is crystallized and transformed to the vanadium dioxide layer 111, the vanadium dioxide layer 111 has a contraction stress because of the smaller lattice, and the carbon nanotube layer 110 has an anti-contraction stress. When the contraction stress of the vanadium dioxide layer 111 is greater than the maximum anti-contraction stress of the carbon nanotube layer 110, the $VO_2$/CNT composite would bend toward the side of the vanadium dioxide layer 111. Thus, the original state of the actuator 11 is curved. When the contraction stress of the vanadium dioxide layer 111 is less than or equal to the maximum anti-contraction stress of the carbon nanotube layer 110, the $VO_2$/CNT composite would be planar shaped. The contraction stress of the vanadium dioxide layer 111 and the anti-contraction stress of the carbon nanotube layer 110 are related to the thicknesses of the vanadium dioxide layer 111 and the carbon nanotube layer 110, respectively. The original state of the actuator 11 can be controlled by changing the thicknesses of the vanadium dioxide layer 111 and the carbon nanotube layer 110.

In another exemplary embodiment, the carbon nanotube layer 110 is formed by cross stacking 50 drawn carbon nanotube films. The W—$VO_x$ (W doped $VO_x$) layer 112 is deposited on a surface of the 50-layer cross-stacked drawn carbon nanotube films by DC magnetron sputtering. The DC magnetron sputtering system has a vanadium/tungsten mixed metal target with 1.5% tungsten by atom number. The sputtering is carried out with flowing gas mixtures of 49.5 sccm Ar and 0.5 sccm $O_2$, under 0.6 Pa, for 30 minutes, at DC power of 60 W, and at room temperature. After the W—VO$_x$ layer 112 deposition, the W—VO$_x$/CNT composite is annealed in low-pressure pure O$_2$ atmosphere under 4.5×10$^{-2}$ mbar at 450° C. for 10 minutes to crystallize into a W—VO$_2$/CNT composite.

Figure 5:
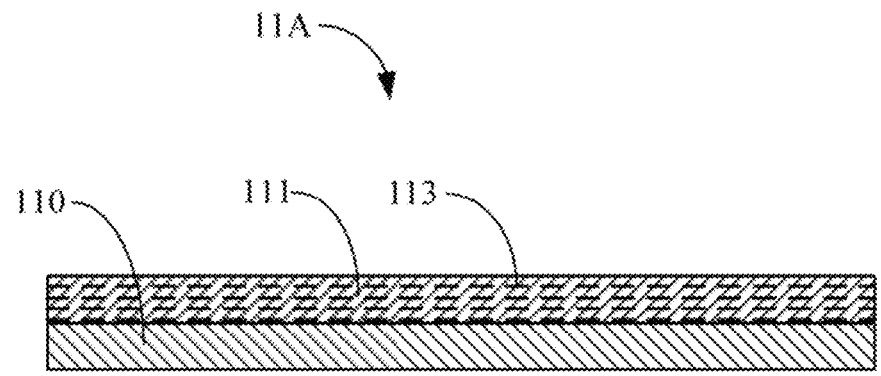
FIG. 5 is a sectional view of a second exemplary embodiment of the actuator.

Referring to FIG. 5, an actuator 11A of the second exemplary embodiment is provided. The actuator 11A includes a carbon nanotube layer 110 and a vanadium dioxide layer 111 stacked with each other to form a VO$_2$/CNT composite.

The actuator 11A of the second exemplary embodiment is similar to the actuator 11 of the first exemplary embodiment except that at least one carbon nanotube film 113 is located and dispersed in the vanadium dioxide layer 111 and spaced apart from the carbon nanotube layer 110. When a plurality of carbon nanotube films 113 are located and dispersed in the vanadium dioxide layer 111, the plurality of carbon nanotube films 113 are spaced apart from each other.

When a laser is radiated on the actuator 11A from the side of the carbon nanotube layer 110, some laser, that pass through the carbon nanotube layer 110, would be absorbed by the at least one carbon nanotube film 113 and converted to heat and heat up the vanadium dioxide layer 111. The thickness of the carbon nanotube film 113 should be small enough and the distance between adjacent two carbon nanotube films 113 should be large enough so that the carbon nanotube film 113 can shrink following the shrinkage of the vanadium dioxide layer 111. Thus, the shrinkage of the vanadium dioxide layer 111 would not be affected by the carbon nanotube film 113. In one exemplary embodiment, the carbon nanotube film 113 is drawn carbon nanotube film having a thickness less than 30 nanometers. When a plurality of carbon nanotube films 113 are located in the vanadium dioxide layer 111, the distance between every two adjacent carbon nanotube films 113 is greater than 30 nanometers.

Figure 6:
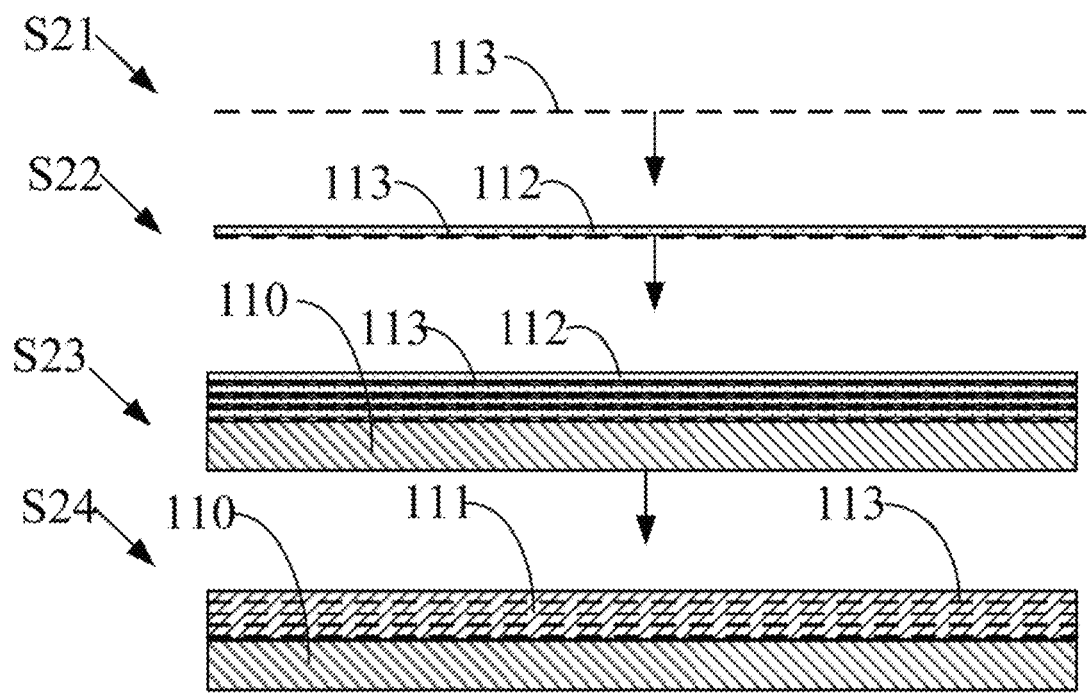
FIG. 6 is a flowchart showing a second exemplary embodiment of a method for making the actuator of FIG. 5.

Referring to FIG. 6, a method for making the actuator 11A of the second exemplary embodiment comprises:

step (S21), providing a plurality of carbon nanotube films 113;

step (S22), depositing a VO$_x$ layer 112 on each of the plurality of carbon nanotube films 113 to form a plurality of preform composite layers;

step (S23), stacking the plurality of preform composite layers on the carbon nanotube layer 110 to form a VO$_x$/CNT composite; and step (S24), annealing the VO$_x$/CNT composite in low-pressure oxygen atmosphere to form a VO$_2$/CNT composite, where the VO$_x$ layer 112 is transformed to the vanadium dioxide layer 111.

In steps (S22) and (S24), the methods for depositing a VO$_x$ layer 112 and annealing the VO$_x$/CNT composite is the same as the above steps (S12) and (S14). In step (S22), the VO$_x$ layer 112 is deposited on two opposite surfaces of the carbon nanotube film 113 and filled in the micropores of the carbon nanotube film 113. Each carbon nanotube of the carbon nanotube film 113 is wrapped by the VO$_x$ layer 112. Thus, the plurality of VO$_x$ layers 112 would form an integrated vanadium dioxide layer 111 after annealing. The plurality of carbon nanotube films 113 are located in the vanadium dioxide layer 111 and spaced apart from each other.

Figure 7:
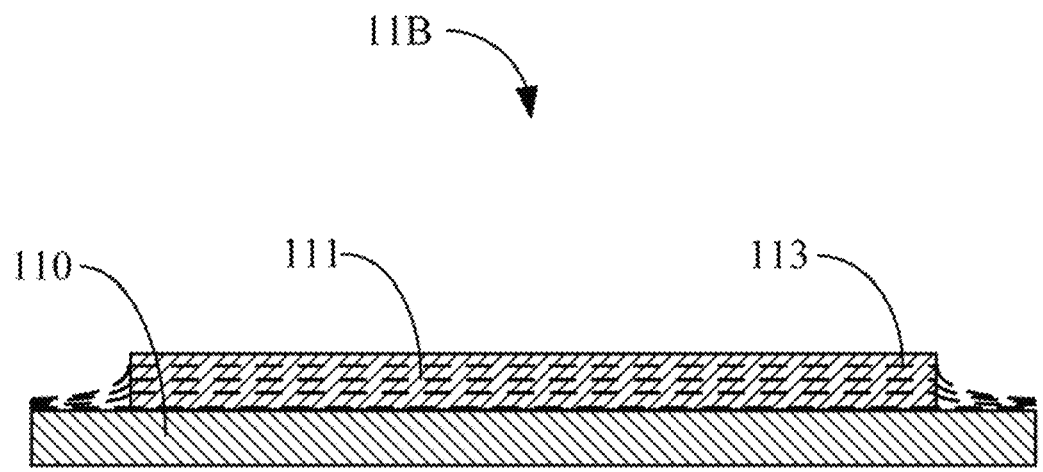
FIG. 7 is a sectional view of a third exemplary embodiment of the actuator.

Referring to FIG. 7, an actuator 11B of the third exemplary embodiment is provided. The actuator 11B includes a carbon nanotube layer 110, a vanadium dioxide layer 111 stacked on the carbon nanotube layer 110, and a plurality of carbon nanotube films 113 located in the vanadium dioxide layer 111.

The actuator 11B of the third exemplary embodiment is similar to the actuator 11A of the second exemplary embodiment except that the carbon nanotube film 113 is larger than the vanadium dioxide layer 111 along a direction perpendicular to the thickness direction of the vanadium dioxide layer 111. Thus, a portion of the carbon nanotube film 113 extends out of the vanadium dioxide layer 111 to form an outside portion. The plurality of carbon nanotube films 113 have a plurality of outside portions staked and in direct contact with each other. The outside portion of the carbon nanotube film 113 can be used to contact with electrodes that can be used to supply electric current to the carbon nanotube film 113 to generate heat.

In one exemplary embodiment, the carbon nanotube layer 110 is also larger than the vanadium dioxide layer 111 along the direction perpendicular to the thickness direction of the vanadium dioxide layer 111. The plurality of outside portions are staked with each other and in direct contact with the edge of the carbon nanotube layer 110. Thus, the electric current can be simultaneously supplied to both the carbon nanotube film 113 and the carbon nanotube layer 110 through two spaced electrodes connected to the outside portions. The heat generated from laser absorbed by the carbon nanotube layer 110 can be conducted to the vanadium dioxide layer 111 through the plurality of carbon nanotube films 113. When the size of the carbon nanotube layer 110 is less than the size of the carbon nanotube film 113, the outside portion of the carbon nanotube film 113 can be folded on the back side of the carbon nanotube layer 110 so that there is a greater contacting surface between the outside portion of the carbon nanotube film 113 and the carbon nanotube layer 110.

Figure 8:
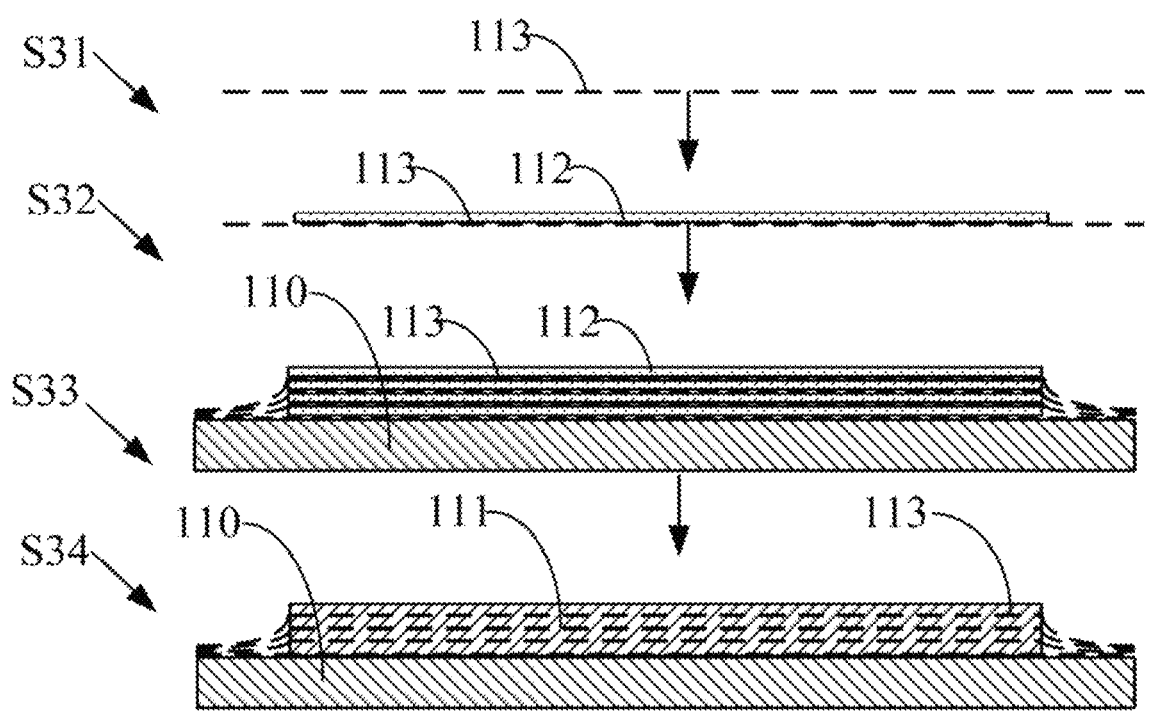
FIG. 8 is a flowchart showing a third exemplary embodiment of a method for making the actuator of FIG. 7.

Referring to FIG. 8, a method for making the actuator 11B of the third exemplary embodiment comprises:

step (S31), providing a plurality of carbon nanotube films 113;

step (S32), depositing a VO$_x$ layer 112 on each of the plurality of carbon nanotube films 113 to form a plurality of preform composite layers, where the size of the VO$_x$ layer 112 is less than the size of the carbon nanotube film 113;

step (S33), stacking the plurality of preform composite layers on the carbon nanotube layer 110 to form a VO$_x$/CNT composite; and step (S34), annealing the VO$_x$/CNT composite in low-pressure oxygen atmosphere to form a VO$_2$/CNT composite, where the VO$_x$ layer 112 is transformed to the vanadium dioxide layer 111, where a portion of each carbon nanotube film 113 extends out of the vanadium dioxide layer 111.

After step (S34), mechanical pressing or organic solvent treating can be performed to allow the outside portion of the carbon nanotube film 113 and the edge of the carbon nanotube layer 110 to be in direct contact with each other. The organic solvent can be dropped on the carbon nanotube film 113 and the carbon nanotube layer 110. The outside portion of the carbon nanotube film 113 and the edge of the carbon nanotube layer 110 would be attached to each other after the organic solvent is volatilized. The organic solvent can be volatile solvent, such as ethanol, methanol, acetone, dichloroethane, chloroform, or mixtures thereof. In one exemplary embodiment, the organic solvent is ethanol.

Figure 9:
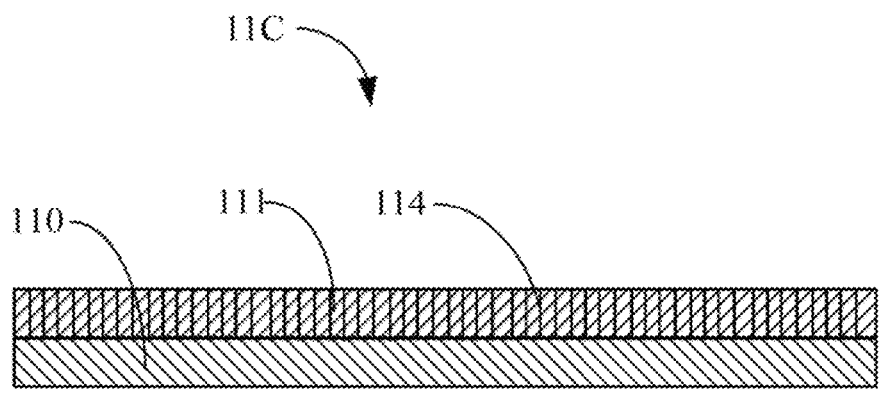
FIG. 9 is a sectional view of a fourth exemplary embodiment of the actuator.

Referring to FIG. 9, an actuator 11C of the fourth exemplary embodiment is provided. The actuator 11C includes a carbon nanotube layer 110 and a vanadium dioxide layer 111 stacked on the carbon nanotube layer 110.

The actuator 11C of the fourth exemplary embodiment is similar to the actuator 11 of the first exemplary embodiment except that a carbon nanotube array 114 is located in the vanadium dioxide layer 111. The carbon nanotube array 114 includes a plurality of carbon nanotubes substantially parallel to and spaced apart from each other. The vanadium dioxide layer 111 is filled in the spaces of the carbon nanotube array 114.

The carbon nanotubes in the carbon nanotube array 114 are perpendicular to the carbon nanotube layer 110. One end of each of the carbon nanotubes in the carbon nanotube array 114 can be exposed from the bottom surface of the vanadium dioxide layer 111 and in direct contact with the top surface of the carbon nanotube layer 110, and the other end of each of the carbon nanotubes in the carbon nanotube array 114 can be exposed from the top surface of the vanadium dioxide layer 111. The heat generated from laser absorbed by the carbon nanotube layer 110 can be conducted to the vanadium dioxide layer 111 through the carbon nanotube array 114 more effectively since the thermal conductivity of the carbon nanotubes along length direction is much better than that along the radial direction. Because the carbon nanotubes in the carbon nanotube array 114 are spaced apart from each other along the in-plane directions that are perpendicular to the thickness direction of the vanadium dioxide layer 111, the carbon nanotube array 114 would shrink along in-plane directions following the shrinkage of the vanadium dioxide layer 111. Thus, the shrinkage of the vanadium dioxide layer 111 is almost not affected by the carbon nanotube array 114.

Figure 10:
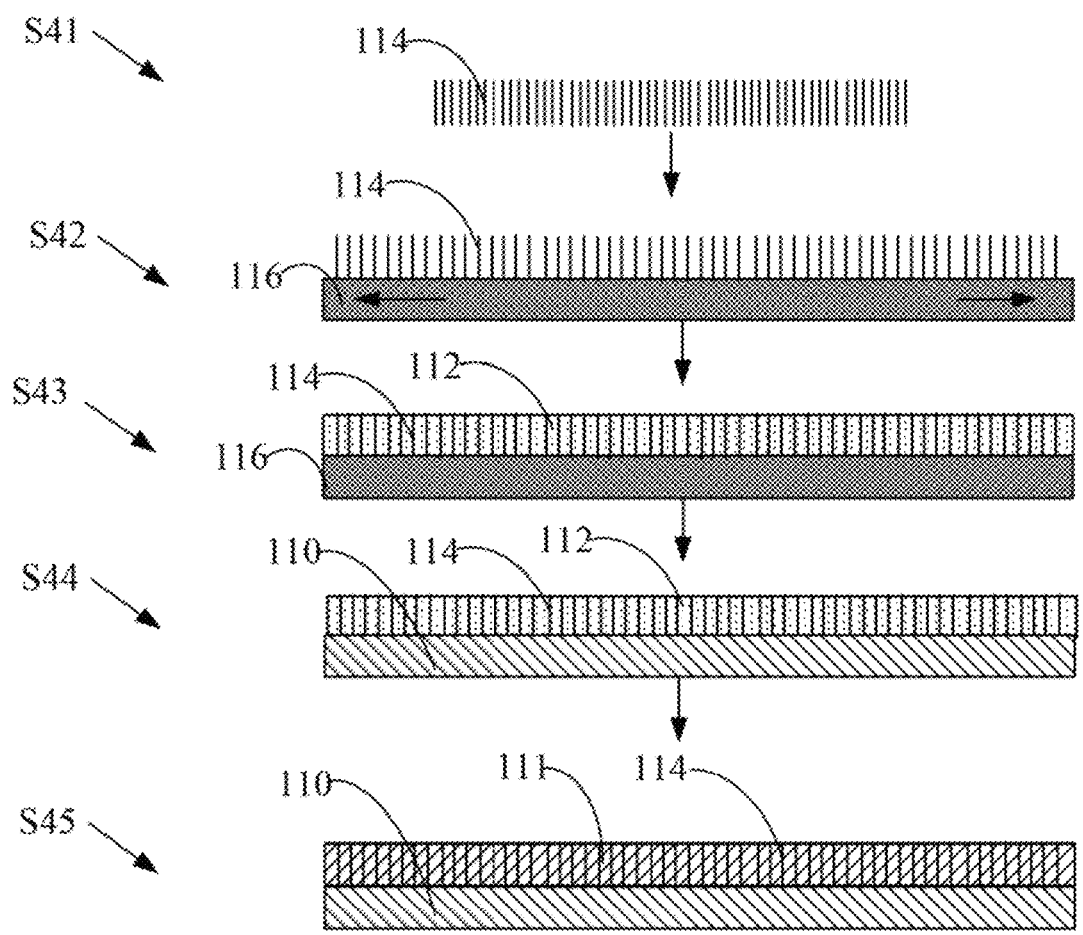
FIG. 10 is a flowchart showing a fourth exemplary embodiment of a method for making the actuator of FIG. 9.

Referring to FIG. 10, a method for making the actuator 11C of the fourth exemplary embodiment comprises:

step (S41), providing a carbon nanotube array 114 including a plurality of carbon nanotubes substantially parallel to each other;

step (S42), stretching the carbon nanotube array 114 along a direction perpendicular to the length direction of the plurality of carbon nanotubes;

step (S43), depositing a $VO_x$ layer 112 on the carbon nanotube array 114 to form a preform composite layer, where the $VO_x$ layer 112 is filled in the spaces of the carbon nanotube array 114;

step (S44), stacking the preform composite layer on the carbon nanotube layer 110 to form a $VO_x$/CNT composite; and step (S45), annealing the $VO_x$/CNT composite in low-pressure oxygen atmosphere to form a $VO_2$/CNT composite, where the $VO_x$ layer 112 is transformed to the vanadium dioxide layer 111.

In step (S41), the carbon nanotube array 114 can be grown on a silicon wafer by CVD. The carbon nanotubes in the carbon nanotube array 114 grown on the silicon wafer has very small spaces therebetween. Thus, it is hard to fill the $VO_x$ layer 112 in the spaces of the carbon nanotube array 114.

In step (S42), the stretching the carbon nanotube array 114 can enlarge the spaces of the carbon nanotube array 114. The carbon nanotube array 114 can be peeled off from the silicon wafer by an elastic adhesive tape 116. Thus, the carbon nanotube array 114 is transformed on the elastic adhesive tape 116 and stretched by drawing the elastic adhesive tape 116 along two opposite directions.

In step (S43), the carbon nanotube array 114 is continuously stretched during depositing the $VO_x$ layer 112. Thus, the $VO_x$ layer 112 is filled in the spaces of the carbon nanotube array 114.

Figure 11:
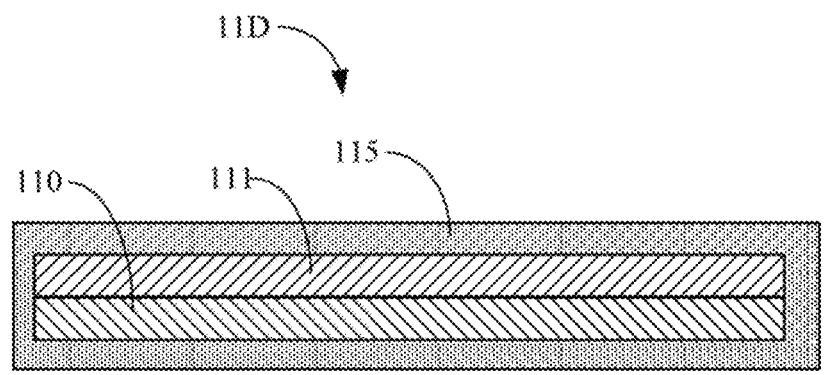
FIG. 11 is a sectional view of a fifth exemplary embodiment of the actuator.

Referring to FIG. 11, an actuator 11D of the fifth exemplary embodiment is provided. The actuator 11D includes a carbon nanotube layer 110 and a vanadium dioxide layer 111 stacked on the carbon nanotube layer 110.

The actuator 11D of the fifth exemplary embodiment is similar to the actuator 11 of the first exemplary embodiment except that a flexible protection layer 115 is located on the surface of the carbon nanotube layer 110 and/or the surface of the vanadium dioxide layer 111. In one exemplary embodiment, the carbon nanotube layer 110 and the vanadium dioxide layer 111 are entirely enveloped by the flexible protection layer 115.

The flexible protection layer 115 prevents the vanadium dioxide layer 111 from being corroded and prevents the carbon nanotube layer 110 from absorbing impurity. The flexible protection layer 115 can be a polymer coating or a silicon rubber sheath. The portion of the flexible protection layer 115, that is in direct contact with the vanadium dioxide layer 111, have small thickness and better elasticity so that the portion of the flexible protection layer 115 can shrink following the shrinkage of the vanadium dioxide layer 111. In one exemplary embodiment, the carbon nanotube layer 110 and the vanadium dioxide layer 111 are entirely enveloped by the silicon rubber sheath.

The method for making the actuator 11D of the fifth exemplary embodiment is similar to the method for making the actuator 11 of the first exemplary embodiment except that further including a step of applying the flexible protection layer 115.

Figure 12:
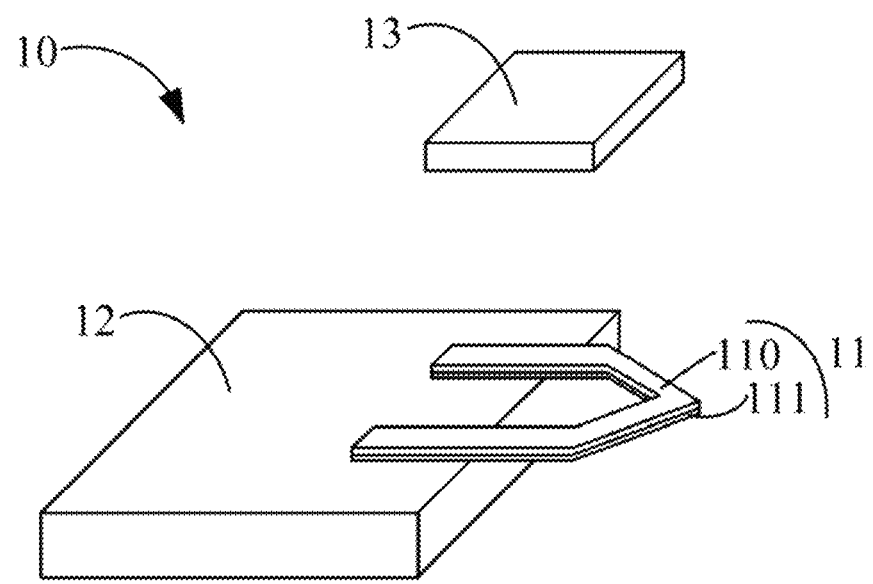
FIG. 12 is a sectional view of a sixth exemplary embodiment of the actuator.

Referring to FIG. 12, an actuating system 10 of the sixth exemplary embodiment is provided. The actuating system 10 includes an actuator 11, a support 12, and an activating device 13. The actuator 11 includes a carbon nanotube layer 110 and a vanadium dioxide layer 111 stacked on the carbon nanotube layer 110. The actuator 11 can also be replaced by other actuators described above.

The actuator 11 has a curved strip-shaped. Two opposite ends of the actuator 11 are fixed on the support 12, and the middle portion of the actuator 11 are suspended by extending out of the support 12. The actuator 11 can also be straight strip-shaped and have only one end fixed on the support 12 and the other end suspended. The activating device 13 is spaced apart from the actuator 11 and used to activate the actuator 11 by wireless mode. The activating device 13 can be located on a side of the carbon nanotube layer 110. The activating device 13 can be a light source. In one exemplary embodiment, the middle portion of the actuator 11 are curved to form a pointed shape. The activating device 13 is a laser device and can be used to apply laser pulse. When the activating device 13 emit laser to radiate the actuator 11, the carbon nanotube layer 110 absorbs the laser and convert the laser to heat. The vanadium dioxide layer 111 is heated to the phase transformation temperature and shrinks. The portion of the actuator 11 that is suspended would bend toward the side of the vanadium dioxide layer 111. When the activating device 13 stop radiating the actuator 11, the actuator 11 is cooled and return to original state.

Figure 13:
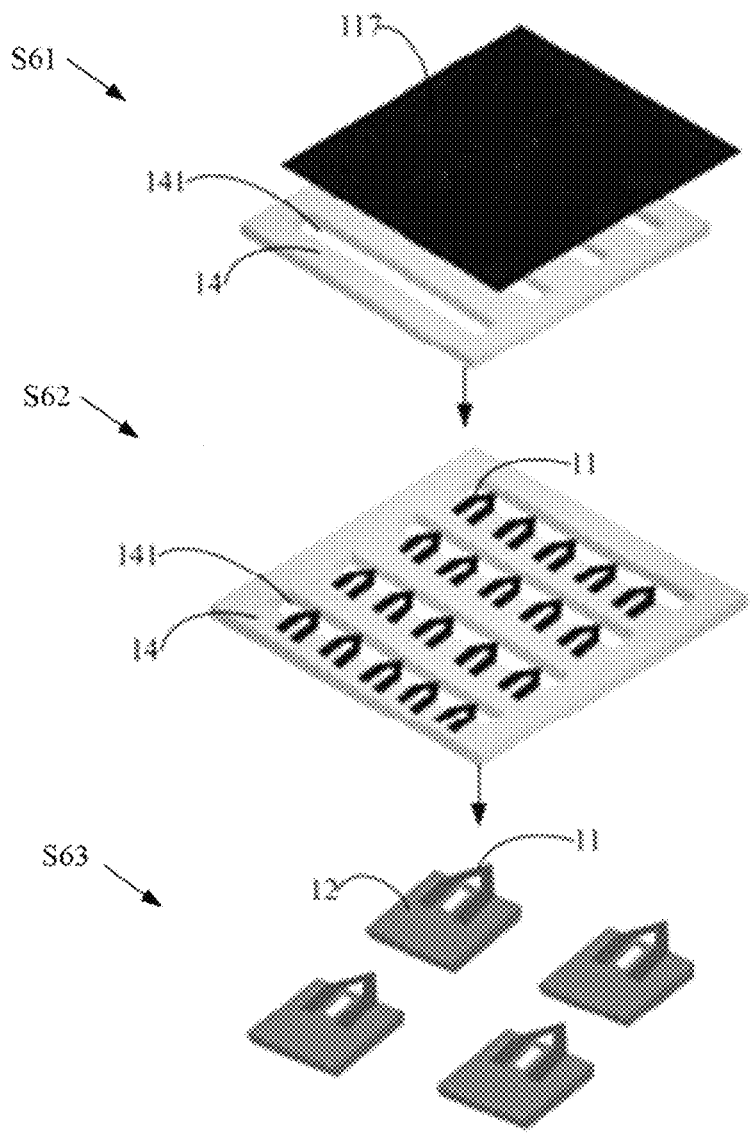
FIG. 13 is a flowchart showing a sixth exemplary embodiment of a method for making the actuator of FIG. 12.

Referring to FIG. 13, a method for making the actuating system 10 of the sixth exemplary embodiment comprises:

step (S61), placing a carbon nanotube layer structure 117 on a plate 14, where the plate 14 defines a plurality of through openings 141 spaced apart from each other, and the carbon nanotube layer structure 117 covers the plurality of through openings 141;

step (S62), patterning the carbon nanotube layer structure 117 to form a plurality of strip-shaped carbon nanotube layer 110, depositing a $VO_x$ layer 112 on each of the plurality of carbon nanotube layers 110, and then transforming the $VO_x$ layer 112 to the vanadium dioxide layer 111 by annealing in low-pressure oxygen atmosphere to form a plurality of actuators 11; and step (S63), cutting the plate 14 to form a plurality of support 12, where each of the plurality of actuators 11 is located on one of the plurality of support 12.

In step (S61), the plurality of through openings 141 can be substantially parallel with each other or arranged to form a two dimensional array. The plurality of through openings 141 can be replaced as strip-shaped grooves or blind holes. In step (S62), the two opposite ends of each of the plurality of strip-shaped carbon nanotube layers 110 are fixed on the surface of the plate 14, and the middle portion of each of the plurality of strip-shaped carbon nanotube layer 110 is suspended through one of the plurality of through openings 141. In one exemplary embodiment, the plate 14 is a $Si_3N_4$ substrate. The carbon nanotube layer structure 117 are patterned by laser scanning.

Figure 14:
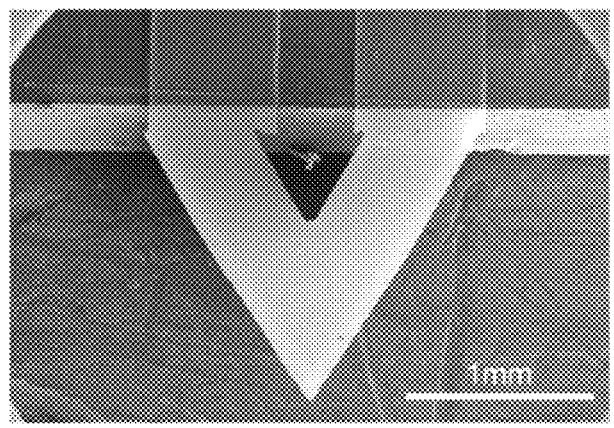
FIG. 14 is a SEM image of the actuator of FIG. 12.
Figure 15:
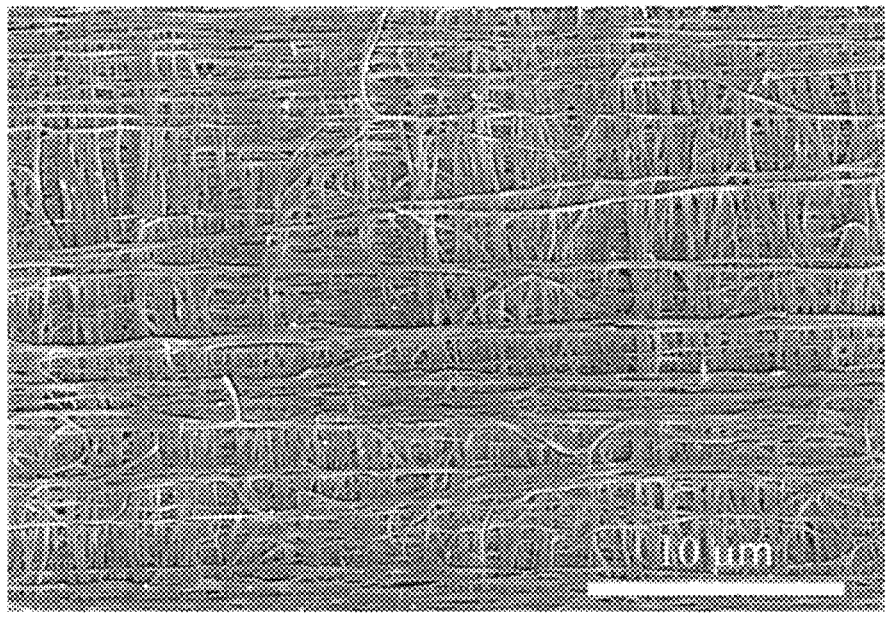
FIG. 15 is a partial enlarged image of the SEM image of FIG. 14.
Figure 16:
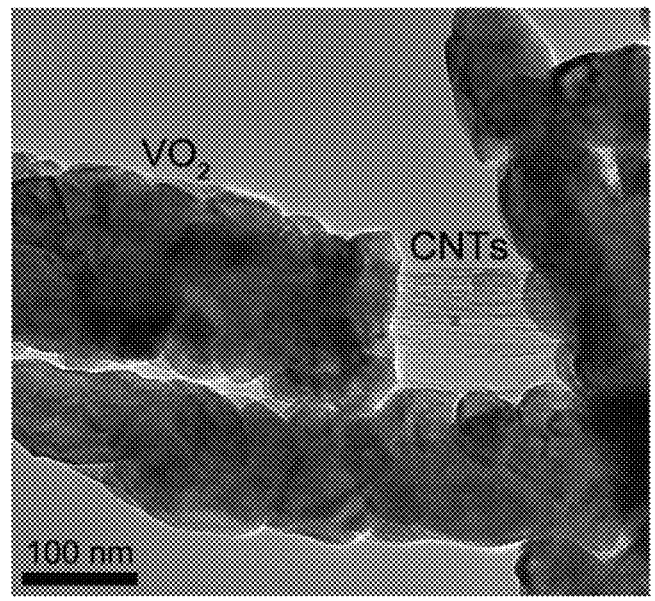
FIG. 16 is a Transmission Electron Microscope (TEM) image of the actuator of FIG. 12.
Figure 17:
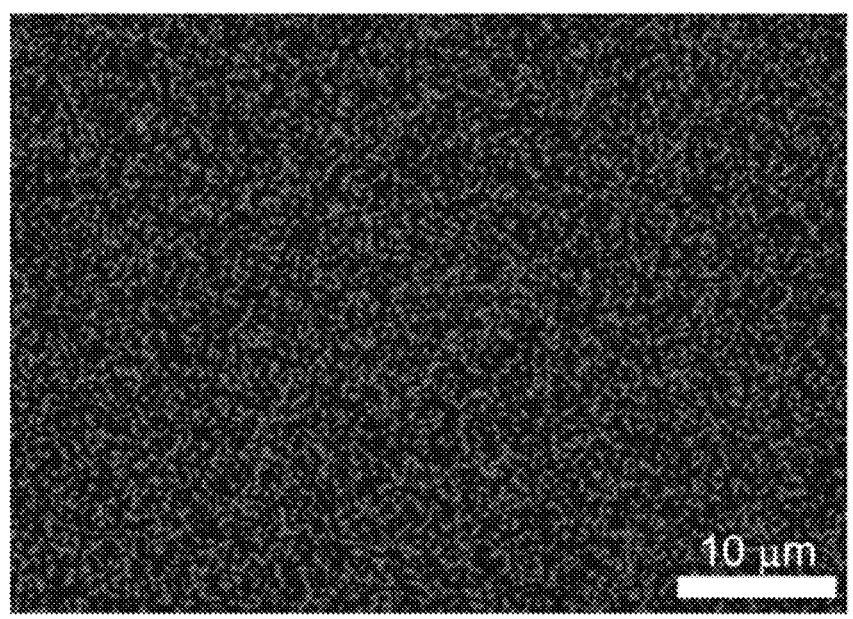
FIG. 17 is an Energy Dispersive X-ray (EDX) of the actuator of FIG. 12.
Figure 18:
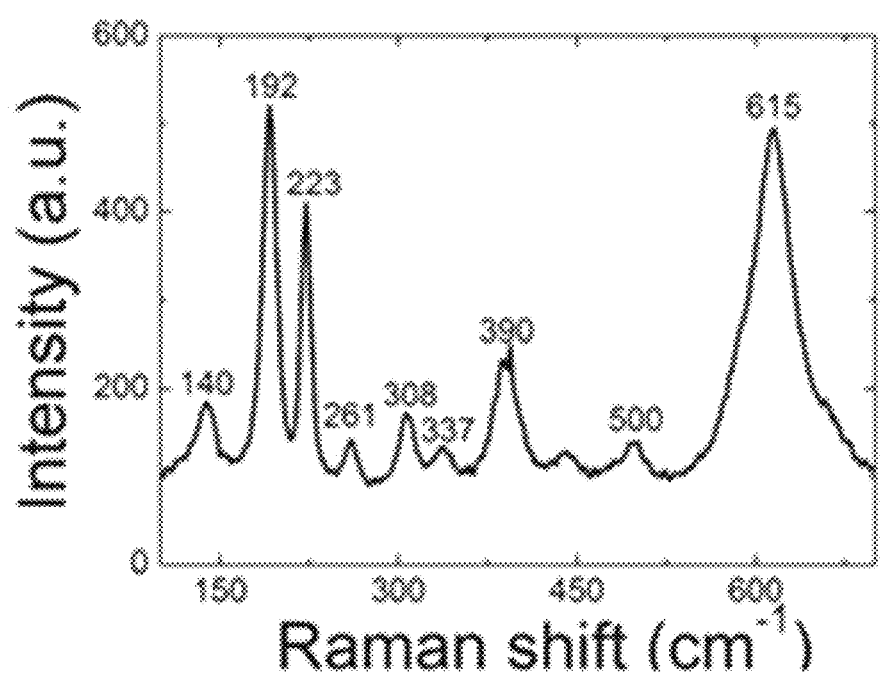
FIG. 18 is a Raman spectrum of the actuator of FIG. 12.

The actuator 11 of the sixth exemplary embodiment is characterized. FIG. 14 is a SEM image of the actuator 11. FIG. 15 is a partial enlarged image of the SEM image of FIG. 14. As shown in FIG. 15, the carbon nanotubes in the carbon nanotube layer 110 are vertically cross with each other, and the vanadium dioxide layer 111 is uniformly dispersed on the carbon nanotube layer 110. FIG. 16 is a TEM image of the actuator 11. As shown in FIG. 15, the vanadium dioxide layer 111 is wrapped on some carbon nanotubes in the carbon nanotube layer 110. FIG. 17 is an EDX of the actuator 11. As shown in FIG. 17, the vanadium dioxide layer 111 is uniformly dispersed on the carbon nanotube layer 110. FIG. 18 is a Raman spectrum of the actuator of FIG. 12. As shown in FIG. 18, the vanadium dioxide layer 111 is in the insulating phase since the peaks 192, 223, and 625 are outstanding. The actuating system 10 of the sixth exemplary embodiment is further tested. The activating device 13 is laser device and used to emit a square wave pulse laser with a power density of 800 mW/cm²-1600 mW/cm². The actuator 11 is radiated by the square wave pulse laser and swings up and down. The attenuation frequency of the actuator 11 is approximately 80 Hz, a response time of the actuator 11 is about 12.5 milliseconds, and the ambient temperature of the actuator 11 is about 43° C. during the test process.

Figure 19:
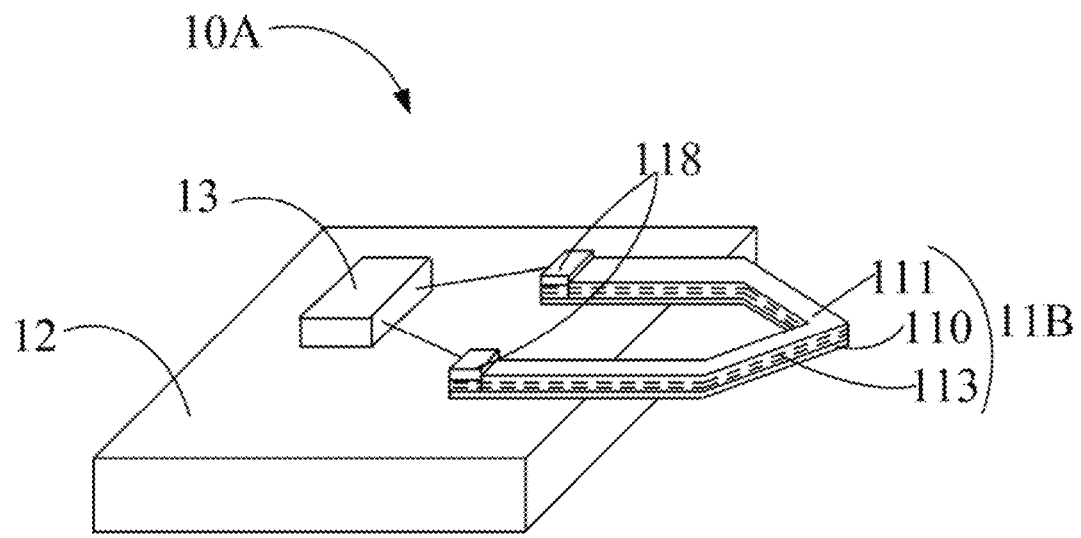
FIG. 19 is a sectional view of a first exemplary embodiment of an actuating system.

Referring to FIG. 19, an actuating system 10A of the first exemplary embodiment is provided. The actuating system 10A includes an actuator 11B, a support 12, and an activating device 13. The actuator 11B includes a carbon nanotube layer 110, a vanadium dioxide layer 111 stacked on the carbon nanotube layer 110, and carbon nanotube films 113 located in the vanadium dioxide layer 111. The actuator 11 can also be replaced by other actuators described above.

The actuating system 10A of the first exemplary embodiment is similar to the actuating system 10 of the sixth exemplary embodiment except that the actuator 11B is used, two electrodes 118 are respectively located on and connected to the two opposite ends of the actuator 11B, and the activating device 13 is a power supply and connected to the two electrodes 118. The power supply can be a direct current power supply or an alternating current power supply. In one exemplary embodiment, the activating device 13 can supply pulse current to the actuator 11B through the two electrodes 118.

The electrodes 118 can be two metal sheets or metal films. The electrodes 118 can be fixed on the carbon nanotube layer 110 by conductive adhesive. The electrodes 118 can also be located on the outside portion of the carbon nanotube film 113 so that the outside portion of the carbon nanotube film 113 is sandwiched between the electrodes 118 and the carbon nanotube layer 110. When the current is supplied to the carbon nanotube layer 110 by the activating device 13. The carbon nanotube layer 110 converts the current to heat to heat the vanadium dioxide layer 111. Thus, the actuator 11B bends. When the activating device 13 stop supplying current, the actuator 11B return to initial state. When the pulse current is supplied to the carbon nanotube layer 110, the actuator 11B swings up and down.

Figure 20:
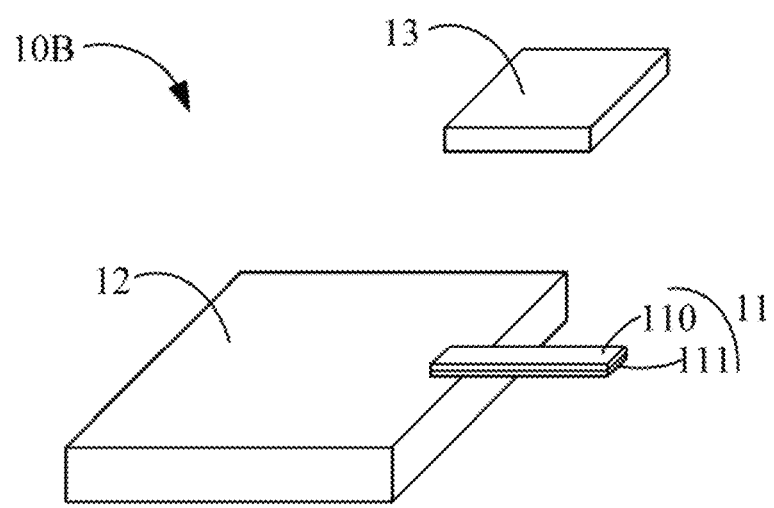
FIG. 20 is a schematic section view of an second exemplary embodiment of an actuating system.

Referring to FIG. 20, an actuating system 10B of the second exemplary embodiment is provided. The actuating system 10B includes an actuator 11, a support 12, and an activating device 13. The actuator 11 includes a carbon nanotube layer 110 and a vanadium dioxide layer 111 stacked on the carbon nanotube layer 110. The actuator 11 can also be replaced by other actuators described above.

The actuating system 10B of the second exemplary embodiment is similar to the actuating system 10 of the sixth exemplary embodiment except that only one end of the actuator 11 is fixed on the support 12, the other end of the actuator 11 is suspended, and the vanadium dioxide layer 111 is a doped with 1.5% tungsten.

Figure 21:
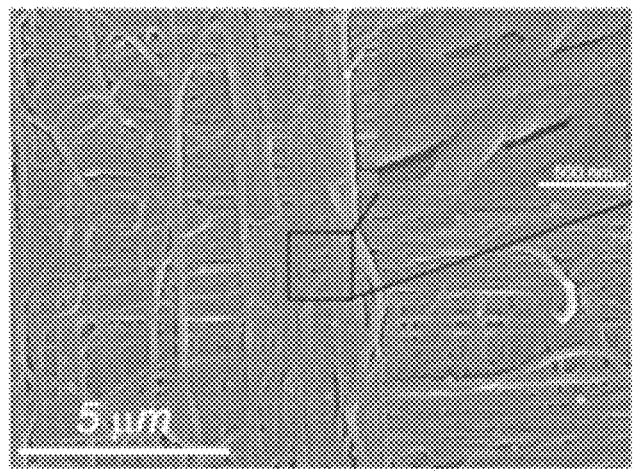
FIG. 21 is a partial enlarged SEM image of an actuator of the actuating system of FIG. 20.
Figure 22:
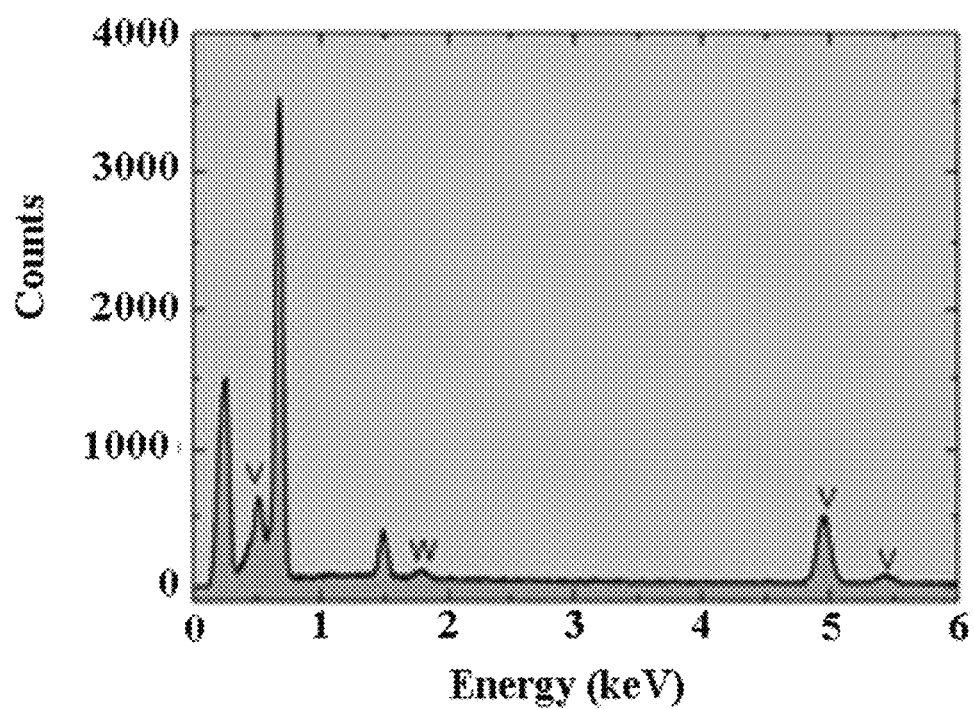
FIG. 22 is an Energy Dispersive Spectrometer (EDS) of an actuator of the actuating system of FIG. 20.
Figure 23:
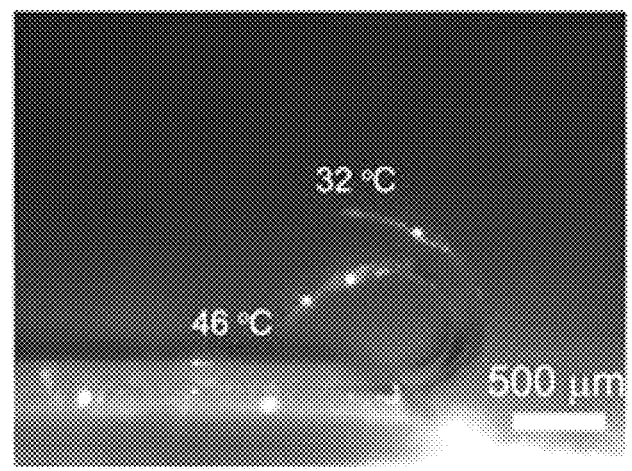
FIG. 23 is an optical image of a curved actuator of the actuating system of FIG. 20 when the actuator is respectively heated to 32° C. and 46° C.
Figure 24:
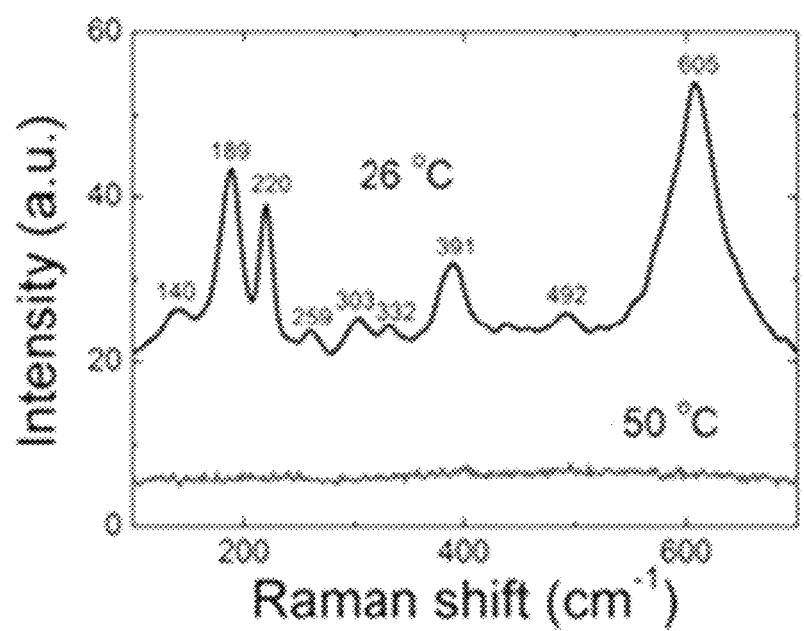
FIG. 24 is a Raman spectrum of an actuator of the actuating system of FIG. 20 respectively at 26° C. and 50° C.

The actuator 11 of the second exemplary embodiment is characterized. FIG. 21 is a partial enlarged SEM image of an actuator 11 of FIG. 20. FIG. 22 is an EDS of an actuator 11 of FIG. 20. As shown in FIG. 22, the tungsten element are doped in the vanadium dioxide layer 111. The actuator 11 of the second exemplary embodiment is further tested. As shown in FIG. 23, the actuator 11 has bended at 32° C. and would further bends at 46° C. FIG. 24 is a Raman spectrum of an actuator 11 of FIG. 20 respectively at 26° C. and 50° C. As shown in FIG. 24, the vanadium dioxide layer 111 is insulating phase at 26° C., and is transited to metallic phase at 50° C. The activating device 13 is laser device and used to emit a square wave pulse laser with a power density of 250 mW/cm²-800 mW/cm². The actuator 11 is radiated by the square wave pulse laser and swings up and down. The attenuation frequency of the actuator 11 is approximately 35 Hz, a response time of the actuator 11 is about 28.5 milliseconds, and the ambient temperature of the actuator 11 is about 9° C. during the test process.

Figure 25:
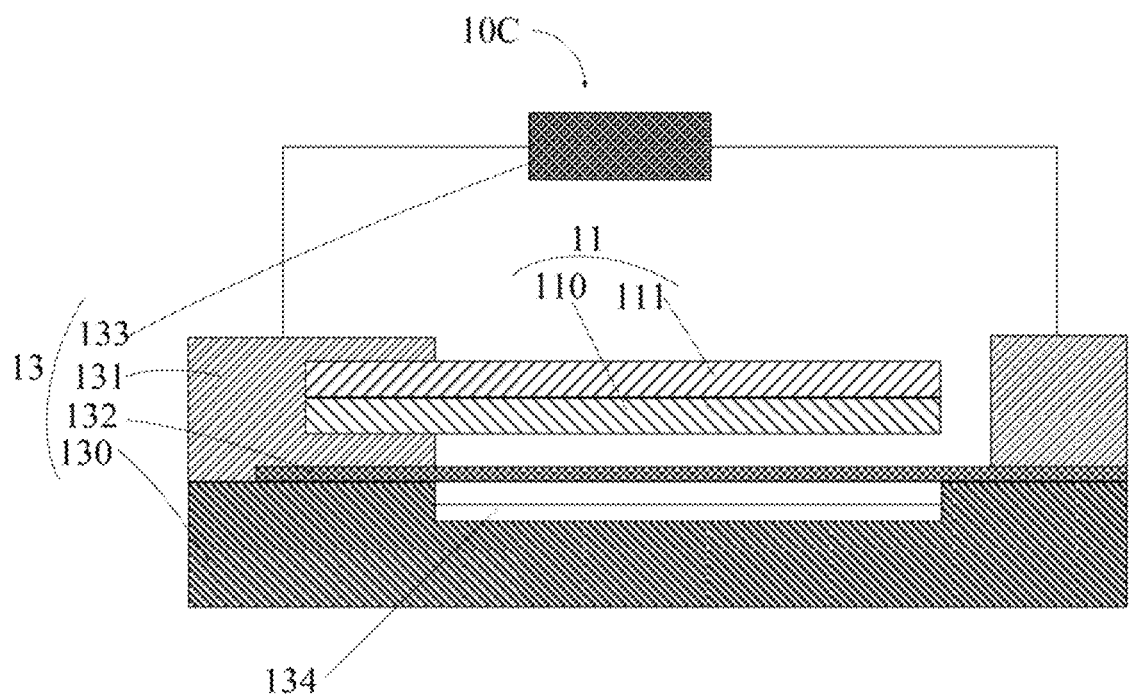
FIG. 25 is a sectional view of a third exemplary embodiment of an actuating system.

Referring to FIG. 25, an actuating system 10C of the third exemplary embodiment is provided. The actuating system 10C includes an actuator 11 and an activating device 13. The actuator 11 includes a carbon nanotube layer 110 and a vanadium dioxide layer 111 stacked on the carbon nanotube layer 110. The actuator 11 can also be replaced by other actuators described above.

The actuating system 10C of the third exemplary embodiment is similar to the actuating system 10 of the sixth exemplary embodiment except that activating device 13 is a heater including a heating element 132 spaced apart from the actuator 11.

In one exemplary embodiment, the activating device 13 includes an insulating substrate 130, two electrodes 131 located on the insulating substrate 130 and spaced apart from each other, a heating element 132 electrically connected to the two electrodes 131, and a power supply 133 respectively electrically connected to the two electrodes 131. The heating element 132 is located on the side of, substantially parallel to, and spaced apart from the carbon nanotube layer 110. The heating element 132 can be a carbon nanotube film or metal wires such as tungsten filament. The heating element 132 is used to heat the actuator 11 by thermal radiation. When the actuating system 10C works in vacuum, the carbon nanotubes heating element 132 can be heated to emit visible light. The insulating substrate 130 can defines a groove and middle portion of the heating element 132 can be suspended through the groove. Two ends of the heating element 132 can be sandwiched between the insulating substrate 130 and the two electrodes 131. One end of the actuator 11 is fixed on one of the two electrodes 131, and the other end of the actuator 11 is suspended above the heating element 132. A reflecting layer 134 can be located on the insulating substrate 130, such as on the bottom surface of the groove, and used to reflect the heat or light from the heating element 132. Thus, the heat or light emitted from the heating element 132 can be absorbed by the carbon nanotube layer 110 effectively.

Figure 26:
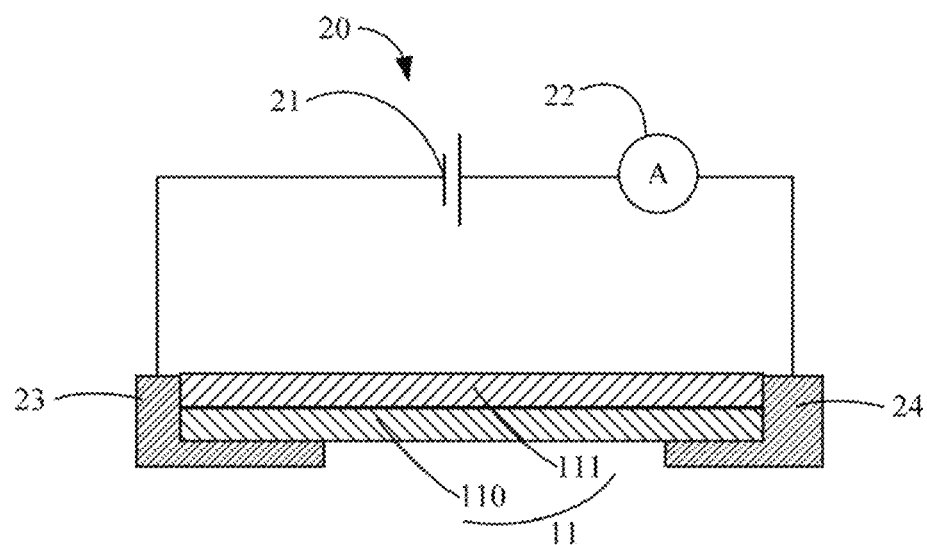
FIG. 26 is a sectional view of a first exemplary embodiment of a temperature sensitive system.

Referring to FIG. 26, a temperature sensitive system 20 of the first exemplary embodiment is provided. The temperature sensitive system 20 includes an actuator 11, a power supply 21, an ammeter 22, a first electrode 23, and a second electrode 24. The actuator 11 includes a carbon nanotube layer 110 and a vanadium dioxide layer 111 stacked on the carbon nanotube layer 110. The actuator 11 can also be replaced by other actuators described above.

The power supply 21 is electrically connected to the first electrode 23 and the second electrode 24. The first end of the actuator 11 is fixed on the first electrode 23, and the carbon nanotube layer 110 is electrically connected to the first electrode 23. The second end of the actuator 11 is in direct contacted with the second electrode 24, and the carbon nanotube layer 110 is electrically connected to the second electrode 24. Thus, the power supply 21, the first electrode 23, the second electrode 24, and the actuator 11 are electrically connected to each other to form a loop circuit. The ammeter 22 is electrically connected in the loop circuit in series.

In operation, the actuator 11 is placed on an object or in an environment. The current supplied to the actuator 11 by the power supply 21 is small enough so that the carbon nanotube layer 110 would not heat the vanadium dioxide layer 111 to the phase transformation temperature. When the temperature of the object or the environment is higher than the phase transformation temperature, the actuator 11 bends, Thus, the second end of the actuator 11 move away and would be spaced apart from the second electrode 24. Thus, the loop circuit is disconnected, and the ammeter 22 shows that there is no current.

Alternatively, the second end of the actuator 11 can be spaced apart from the second electrode 24 so that the loop circuit is disconnected usually. When the actuator 11 bends, the second end of the actuator 11 move toward and would be connected to the second electrode 24. Thus, the loop circuit is formed, and the ammeter 22 shows that there is current.

The ammeter 22 can also be replaced by other electric device that can show the current of the loop circuit, such as a lamp or a voltmeter. The voltmeter should be connected to a resistance in the loop circuit in parallel. The ammeter 22 can also be replaced by an alarm device.

Figure 27:
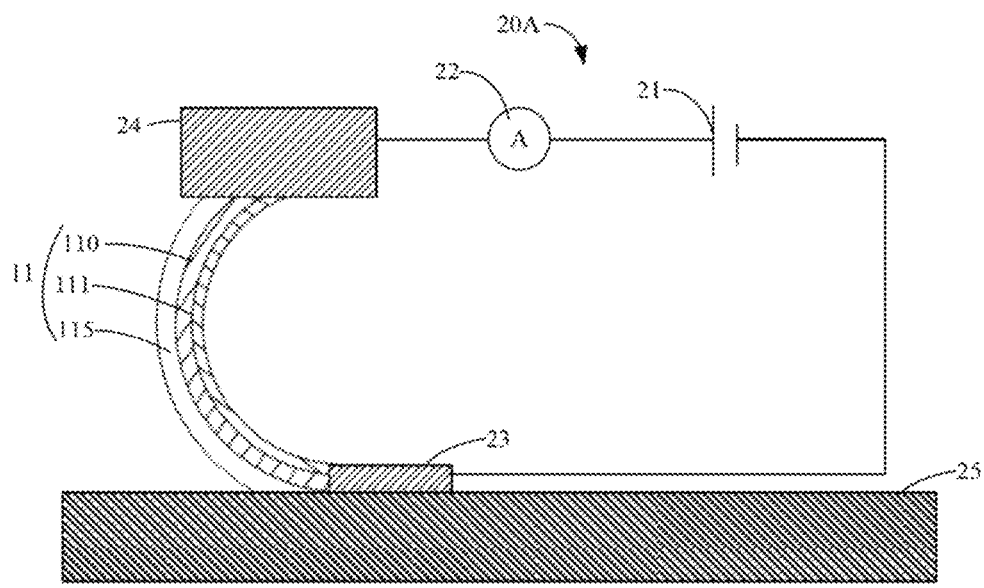
FIG. 27 is a sectional view of a second exemplary embodiment of a temperature sensitive system.

Referring to FIG. 27, a temperature sensitive system 20A of the second exemplary embodiment is provided. The temperature sensitive system 20A includes an actuator 11, a power supply 21, an ammeter 22, a first electrode 23, a second electrode 24, and a thermal conductive substrate 25. The actuator 11 includes a carbon nanotube layer 110 and a vanadium dioxide layer 111 stacked on the carbon nanotube layer 110. The actuator 11 can also be replaced by other actuators described above.

The temperature sensitive system 20A of the second exemplary embodiment is similar to the temperature sensitive system 20 of the first exemplary embodiment except that the first end of the actuator 11 is fixed on the thermal conductive substrate 25 by the first electrode 23. The second end of the actuator 11 is in direct contact with and pressed by the second electrode 24 so that the actuator 11 is usually bended under the pressure of the second electrode 24. The thermal conductive substrate 25 is an insulating ceramic plate. The vanadium dioxide layer 111 is doped with tungsten and has a phase transformation temperature of 37° C. The actuator 11 further includes a flexible protection layer 115 coated on the carbon nanotube layer 110 so that the elasticity of bending the actuator 11 is increased.

In operation, the thermal conductive substrate 25 is attached on the object. When the temperature of the object is higher than the phase transformation temperature, the actuator 11 further bends toward the side of the vanadium dioxide layer 111. Thus, the second end of the actuator 11 move away and would be spaced apart from the second electrode 24. Thus, the loop circuit is disconnected, and the ammeter 22 shows that there is no current. When the temperature of the object is lower than the phase transformation temperature, the actuator 11 would return to the initial state under the elastic force of the actuator 11. Thus, the second end of the actuator 11 move toward and would be connected to the second electrode 24. Thus, the loop circuit is formed, and the ammeter 22 shows that there is current. The flexible protection layer 115 allows the actuator 11 return to the initial state rapidly when temperature of the object is lower than the phase transformation temperature.

Figure 28:
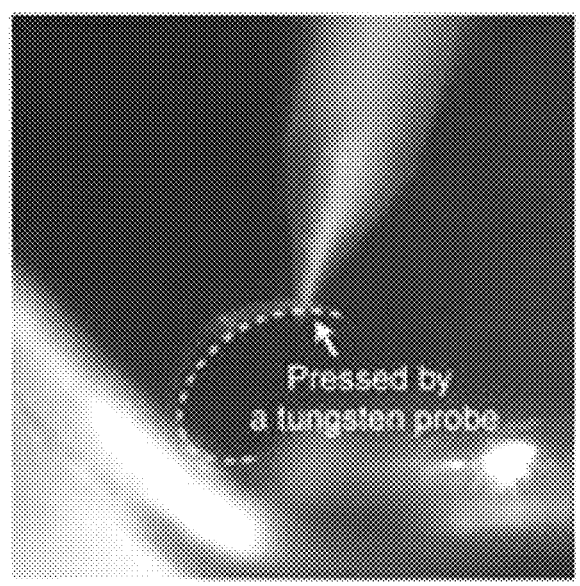
FIG. 28 is a SEM image of an actuator of the temperature sensitive system of FIG. 27.
Figure 29:
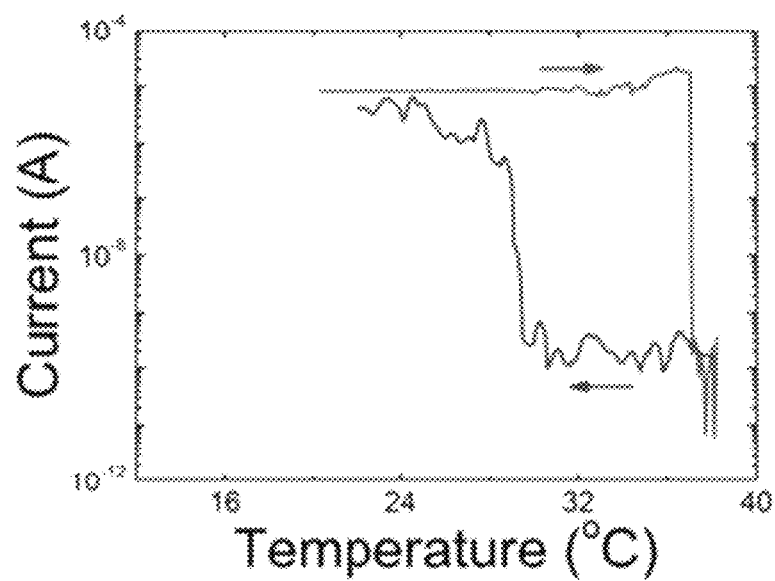
FIG. 29 is a human body temperature test result of the temperature sensitive system of FIG. 27.

FIG. 28 is a SEM image of the actuator 11 of the temperature sensitive system 20A of FIG. 27. As shown in the FIG. 28, the second end of the actuator 11 bends and pressed by the second electrode 24 which is a tungsten probe. FIG. 29 is a human body temperature test result of the temperature sensitive system 20A of FIG. 27. As shown in the FIG. 29, when the human body temperature reaches 37° C., the current of the ammeter 22 suddenly and sharp declines. It represents that the electrical circuit in FIG. 27 cuts off.

Figure 30:
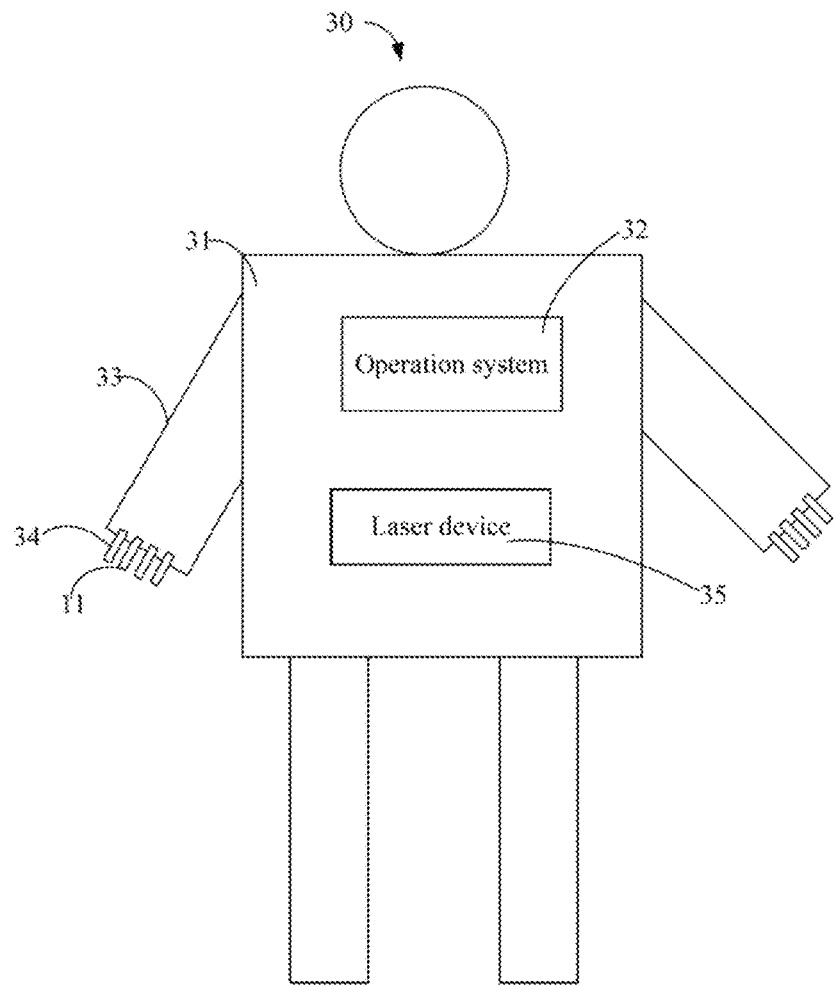
FIG. 30 is a sectional view of a first exemplary embodiment of a robot.

Referring to FIG. 30, a robot 30 of the first exemplary embodiment is provided. The robot 30 includes a body 31 and an operation system 32 loaded on the body 31. The body 31 includes at least one biomimetic upper limb 33 and a laser device 35. The biomimetic upper limb 33 includes an arm and a biomimetic hand 34 connected to the arm. The biomimetic hand 34 is made of the $VO_2$/CNT composite described above. The laser device 35 is used to radiate the biomimetic hand 34.

The shape of the biomimetic hand 34 is not limited and can be designed according to need. The biomimetic hand 34 can have a single biomimetic finger or a plurality of biomimetic fingers. In one exemplary embodiment, the biomimetic hand 34 has four biomimetic fingers spaced apart from each other. Each biomimetic finger is a strip-shaped actuator 11 and includes a carbon nanotube layer 110 and a vanadium dioxide layer 111 stacked on the carbon nanotube layer 110.

Figure 31:
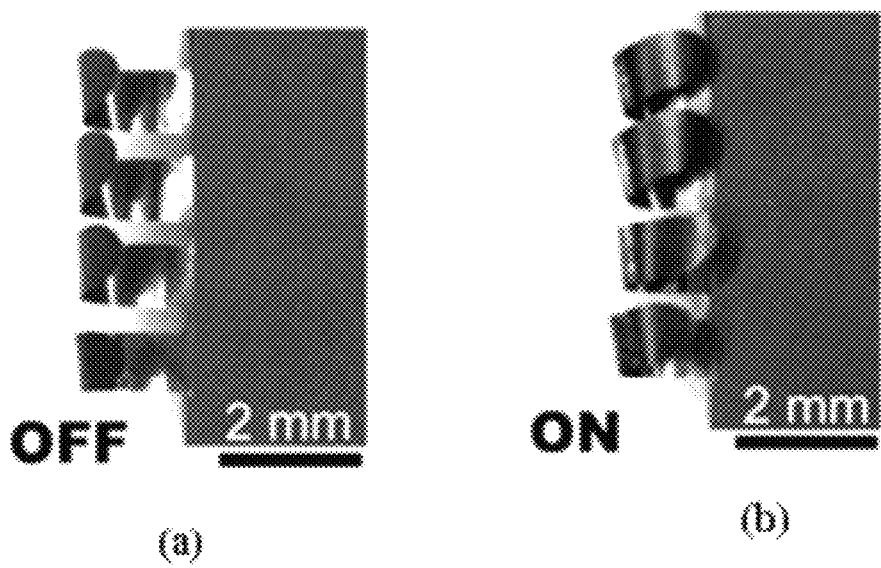
FIG. 31 shows two optical images of a biomimetic hand of the robot of FIG. 30.
Figure 32:
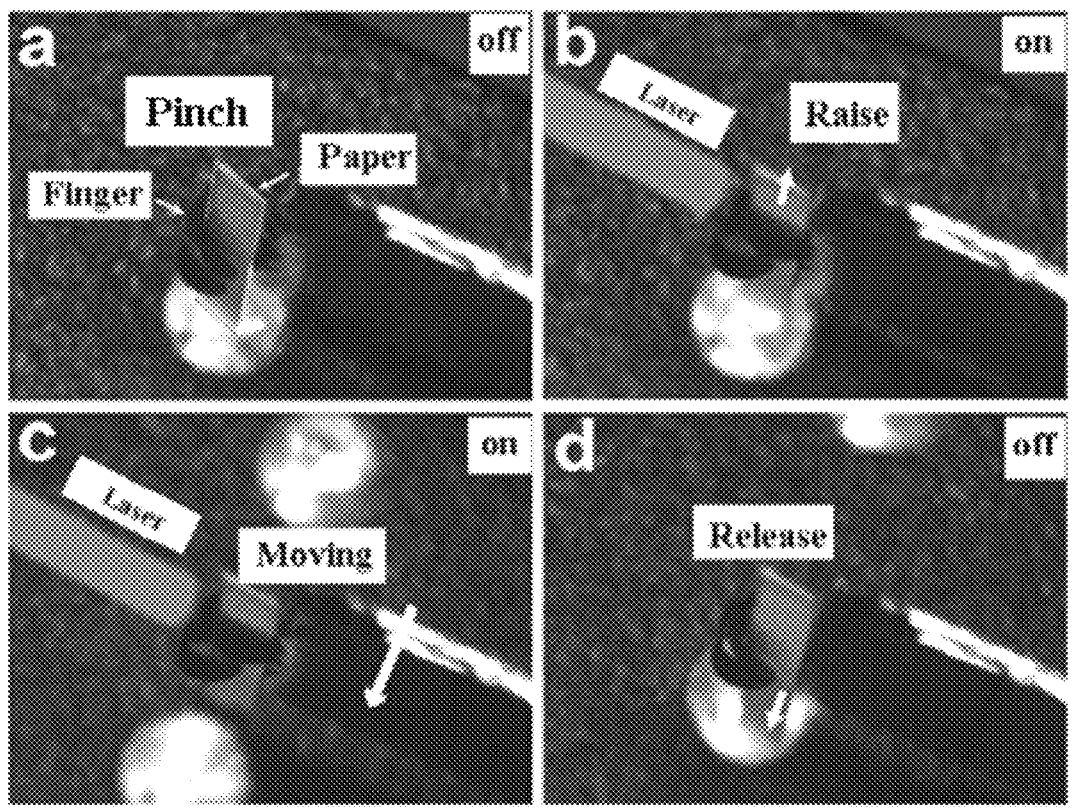
FIG. 32 shows how the biomimetic hand of FIG. 31 moves a paper slip.

FIG. 31 shows two optical images of a biomimetic hand 34 of the robot of FIG. 30. As shown in FIG. 31(a), when the laser device 35 is off, the initial or natural state of the biomimetic hand 34 is that the four fingers are curved but the biomimetic hand 34 is open. As shown in FIG. 31(b), when the laser device 35 is on, the biomimetic hand 34 is closed. FIG. 32 shows how the biomimetic hand 34 moves a paper slip. In FIG. 32(a), the biomimetic hand 34 pinches and takes the paper slip at a first position. In FIG. 32(b), the biomimetic hand 34 raises up the paper slip. In FIG. 32(c), the biomimetic hand 34 moves the paper slip from the first position to the second position. In FIG. 32(d), the biomimetic hand 34 releases and put down the paper slip at the second position.

Figure 33:
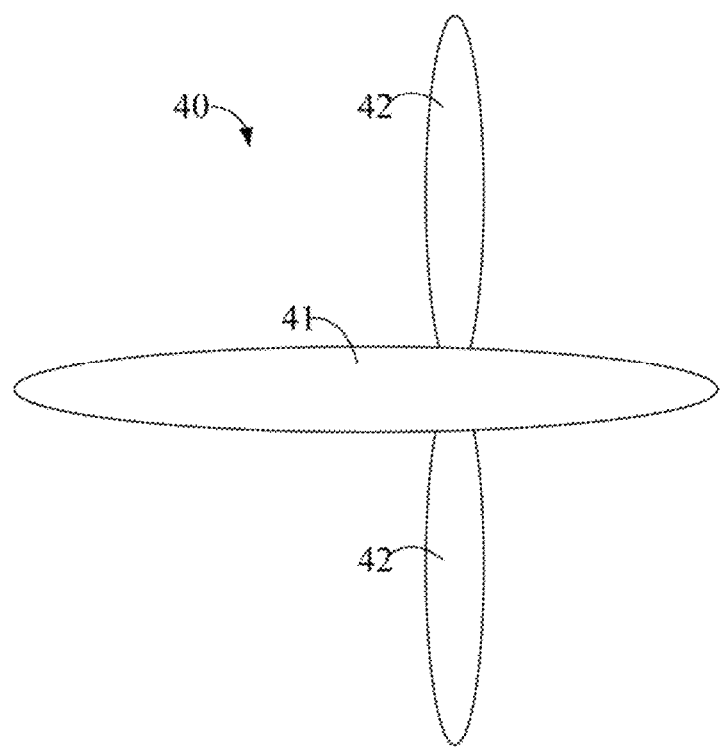
FIG. 33 is a section view of a first exemplary embodiment of a biomimetic insect.

Referring to FIG. 33, a biomimetic insect 40 of the first exemplary embodiment is provided. The biomimetic insect 40 includes a trunk 41 and at least two wings 42 connected to the trunk 41. The two wings 42 are symmetrical. The at least two wings 42 are made by cutting the VO$_2$/CNT composite described above and includes a carbon nanotube layer 110 and a vanadium dioxide layer 111.

Figure 34:
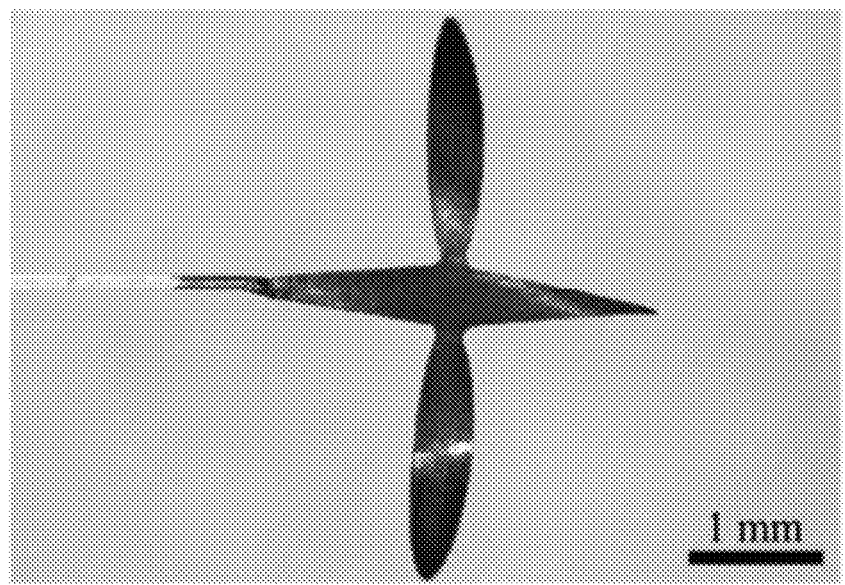
FIG. 34 is an optical image of the biomimetic insect of FIG. 33.
Figure 36:
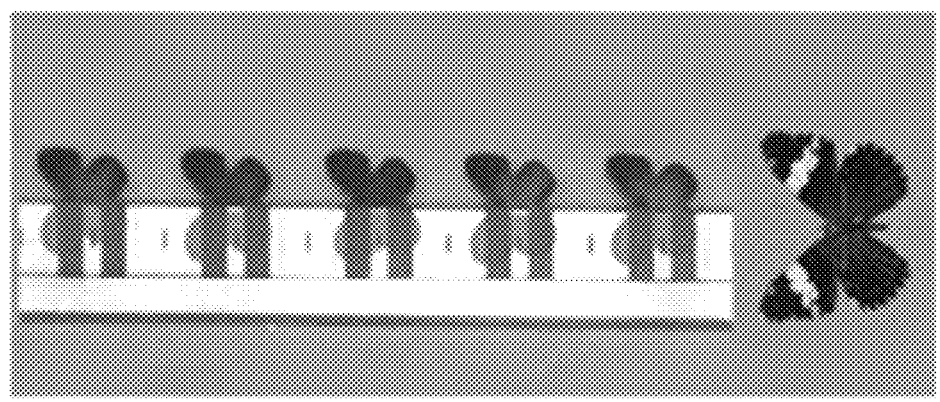
FIG. 36 is an optical image of the second exemplary embodiment of a pluralities of biomimetic butterflies.

The size of the biomimetic insect 40 can be in a range of 1 millimeter to 5 centimeters. The biomimetic insect 40 can be a dragonfly, a butterfly, a mosquito, a fly, or a moths. In one exemplary embodiment, both the trunk 41 and the at least two wings 42 are made of the VO$_2$/CNT composite described above. Thus, as shown in FIGS. 34 and 36, the trunk 41 and the at least two wings 42 can be integrated. The biomimetic insect 40 can be made by directly cutting the VO$_2$/CNT composite to form the insect pattern. The biomimetic insect 40 can also be made by cutting the carbon nanotube layer 110 to form the insect pattern and then applying the vanadium dioxide layer 111 thereon. As shown in FIG. 36, a pluralities of biomimetic butterflies are made by patterning the same VO$_2$/CNT composite layer.

Figure 35:
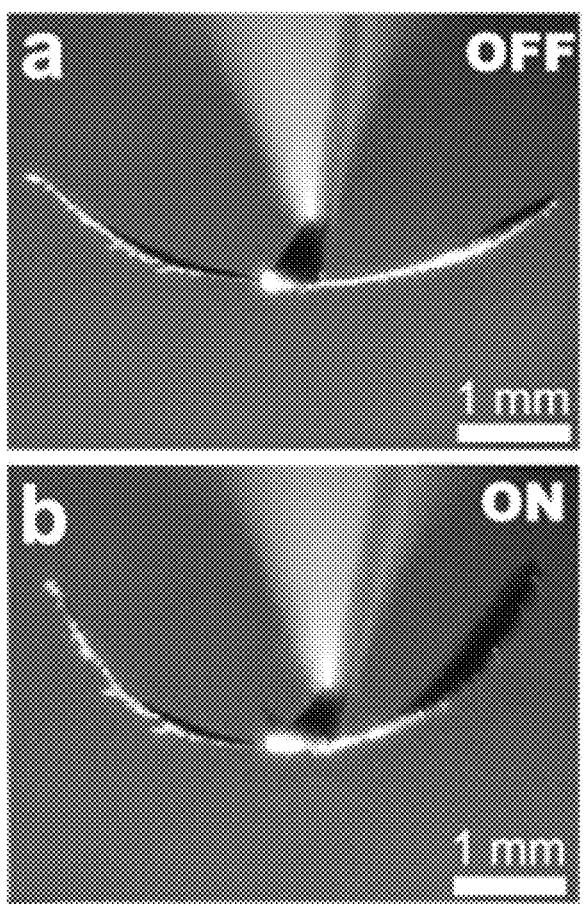
FIG. 35 shows how the biomimetic insect of FIG. 33 wings.

As shown in FIG. 35, when a square wave pulse laser with a frequency of 10 Hz is applied to the biomimetic insect 40, the biomimetic insect 40 flaps wings. The frequency, that the biomimetic insect 40 flaps wings, is about 80 Hz.

Alternatively, the trunk 41 can also consists of other material, such as polymer or rubber. The two wings 42 are two strip-shaped actuator 11 and fixed on the trunk 41. The biomimetic insect 40 may includes some sensors, such as micro camera, located in the trunk 41. The biomimetic insect 40 are good tools for spying purposes in military applications.

It is to be understood that the above-described exemplary embodiments are intended to illustrate rather than limit the disclosure. Any elements described in accordance with any exemplary embodiments is understood that they can be used in addition or substituted in other exemplary embodiments. Exemplary embodiments can also be used together. Variations may be made to the exemplary embodiments without departing from the spirit of the disclosure. The above-described exemplary embodiments illustrate the scope of the disclosure but do not restrict the scope of the disclosure.

Depending on the exemplary embodiment, certain of the steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

What is claimed is:

1. A biomimetic limb comprising:
an arm; and
a biomimetic hand connected to the arm and comprising a biomimetic finger, wherein the biomimetic finger comprises a carbon nanotube layer and a vanadium dioxide layer on the carbon nanotube layer, and the vanadium dioxide layer is doped with tungsten.

2. The biomimetic limb of claim 1, wherein the biomimetic finger further comprises a carbon nanotube film located in the vanadium dioxide layer and spaced apart from the carbon nanotube layer, wherein a thickness of the carbon nanotube film is less than 30 nanometers.

3. The biomimetic limb of claim 2, wherein the biomimetic finger further comprises a plurality of carbon nanotube film located in the vanadium dioxide layer and spaced apart from each other, wherein a distance between every two adjacent carbon nanotube films is greater than 30 nanometers.

4. The biomimetic limb of claim 2, wherein a portion of the carbon nanotube film extends out of the vanadium dioxide layer to form an outside portion.

5. The biomimetic limb of claim 4, wherein the outside portion is in direct contact with the carbon nanotube layer.

6. The biomimetic limb of claim 1, wherein the biomimetic finger further comprises a carbon nanotube array located in the vanadium dioxide layer, wherein the carbon nanotube array comprises a plurality of carbon nanotubes substantially parallel to and spaced apart from each other, and the plurality of carbon nanotubes is perpendicular to the carbon nanotube layer.

7. The biomimetic limb of claim 6, wherein each of the plurality of carbon nanotubes has one end in direct contact with the carbon nanotube layer.

8. The biomimetic limb of claim 1, wherein the biomimetic finger further comprises a flexible protection layer located on at least one of the carbon nanotube layer and the vanadium dioxide layer.

9. The biomimetic limb of claim 8, wherein the flexible protection layer entirely envelopes the carbon nanotube layer and the vanadium dioxide layer.

10. The biomimetic limb of claim 1, wherein the vanadium dioxide layer is a doped with 1.5% tungsten, and a phase transformation temperature of the vanadium dioxide layer is approximately 34° C.

11. A robot comprising a body and an operation system loaded on the body; wherein the body comprises a biomimetic limb and an activating device, and the biomimetic limb comprises:
an arm; and
a biomimetic hand connected to the arm and comprising a biomimetic finger, wherein the biomimetic finger comprises a carbon nanotube layer and a vanadium dioxide layer on the carbon nanotube layer, and the vanadium dioxide layer is doped with tungsten.

12. The robot of claim 11, wherein the biomimetic finger further comprises a carbon nanotube film located in the vanadium dioxide layer and spaced apart from the carbon nanotube layer, and a thickness of the carbon nanotube film is less than 30 nanometers.

13. The robot of claim 12, wherein a portion of the carbon nanotube film extends out of the vanadium dioxide layer to form an outside portion.

14. The robot of claim 13, wherein the outside portion is in direct contact with the carbon nanotube layer.

15. The robot of claim 11, wherein the biomimetic finger further comprises a carbon nanotube array located in the vanadium dioxide layer, and the carbon nanotube array comprises a plurality of carbon nanotubes substantially parallel to and spaced apart from each other, and the plurality of carbon nanotubes is perpendicular to the carbon nanotube layer.

16. The robot of claim 15, wherein each of the plurality of carbon nanotubes has one end in direct contact with the carbon nanotube layer.

17. The robot of claim 11, wherein the biomimetic finger further comprises a flexible protection layer located on at least one of the carbon nanotube layer and the vanadium dioxide layer.

18. The robot of claim 17, wherein the flexible protection layer entirely envelopes the carbon nanotube layer and the vanadium dioxide layer.

19. The robot of claim 11, wherein the activating device is a laser device, a light source, or a power supply.

20. The robot of claim 11, wherein the vanadium dioxide layer is a doped with 1.5% tungsten, and a phase transformation temperature of the vanadium dioxide layer is approximately 34° C.

\* \* \* \* \*